United States Patent
Harris et al.

(10) Patent No.: US 7,943,141 B2
(45) Date of Patent: May 17, 2011

(54) ACTIVATED POLYOXAZOLINES AND COMPOSITIONS COMPRISING THE SAME

(75) Inventors: J. Milton Harris, Huntsville, AL (US); Michael David Bentley, Huntsville, AL (US); Kunsang Yoon, Madison, AL (US); Zhihao Fang, Madison, AL (US); Francesco Maria Veronese, Padua (IT)

(73) Assignee: Serina Therapeutics, Inc., Huntsville, AL (US)

( * ) Notice: Subject to any disclaimer, the term of this patent is extended or adjusted under 35 U.S.C. 154(b) by 0 days.

(21) Appl. No.: 12/529,001

(22) PCT Filed: Feb. 28, 2008

(86) PCT No.: PCT/US2008/002626
§ 371 (c)(1),
(2), (4) Date: Aug. 27, 2009

(87) PCT Pub. No.: WO2008/106186
PCT Pub. Date: Sep. 4, 2008

(65) Prior Publication Data
US 2010/0069579 A1      Mar. 18, 2010

Related U.S. Application Data

(60) Provisional application No. 60/892,212, filed on Feb. 28, 2007.

(51) Int. Cl.
*A61K 39/385*     (2006.01)

(52) U.S. Cl. ............... 424/194.1; 424/78.08; 424/78.36; 424/78.38; 424/178.1; 424/179.1; 424/193.1; 424/280.1; 525/410; 525/411; 525/417; 525/540; 528/403; 528/417; 528/422; 528/423

(58) Field of Classification Search ............... 424/78.08, 424/78.36, 78.38, 178.1, 179.1, 193.1, 194.1, 424/280.1; 525/410, 411, 417, 540; 528/403, 528/417, 422, 423
See application file for complete search history.

(56) References Cited

U.S. PATENT DOCUMENTS

| | | | |
|---|---|---|---|
| 5,672,662 A * | 9/1997 | Harris et al. | 525/408 |
| 6,890,518 B2 * | 5/2005 | Patton et al. | 424/45 |
| 6,908,963 B2 | 6/2005 | Roberts | |
| 2005/0226843 A1 * | 10/2005 | Bentley | 424/78.27 |
| 2006/0105046 A1 * | 5/2006 | Bentley et al. | 424/486 |

OTHER PUBLICATIONS

Chujo, Y.; Ihara, E.; Kure, S.; Saegusa, T.; Macromolecules, 1993(26), p. 5681-5686.*
Waschinski, C.J.; Tiller, J.C.; Biomacromolecules, 2005(6), p. 235-243.*
Miyamoto, M.; Naka, K.; Shiozaki, M.; Chujo, Y.; Saegusa, T.; Macromolecules, vol. 23 (13), Jun. 25, 1990, p. 3201-3205.*
Velander, et al., Polyoxazoline-peptide adducts that retain antibody activity. Biotechnology and Bioengineering. Dec. 1992, vol. 39.
Tsutumiuchi, et al. Synthesis of polyoxazolin-(glyco)peptide block copolymers by reingopenting polymerization of (sugar-substitued)-alpha-amino acit N0carboxyanhydrides with polyoxazoline macroinitiators. Macromolecules. Jun. 1997, vol. 30, pp. 4013-4017.

* cited by examiner

*Primary Examiner* — David Wu
*Assistant Examiner* — Robert Jones
(74) *Attorney, Agent, or Firm* — Bradley Arant Boult Cummings, LLP

(57) ABSTRACT

The present disclosure provides terminally activated monofunctional POZ derivatives having a range of functional active groups allowing conjugation of the monofunctional POZ derivatives to a variety of target molecules under a wide range of reaction conditions to produce a hydrolytically stable target molecule-POZ conjugate. Furthermore, the present disclosure provides novel methods of synthesis for the disclosed terminally activated monofunctional POZ derivatives and hydrolytically stable target molecule-POZ conjugates created using the disclosed terminally activated monofunctional POZ derivatives.

17 Claims, 4 Drawing Sheets

Initiation
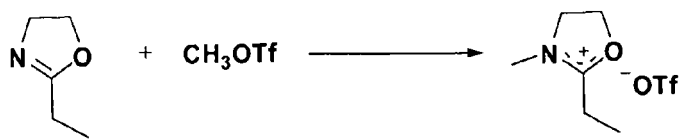
Propagation
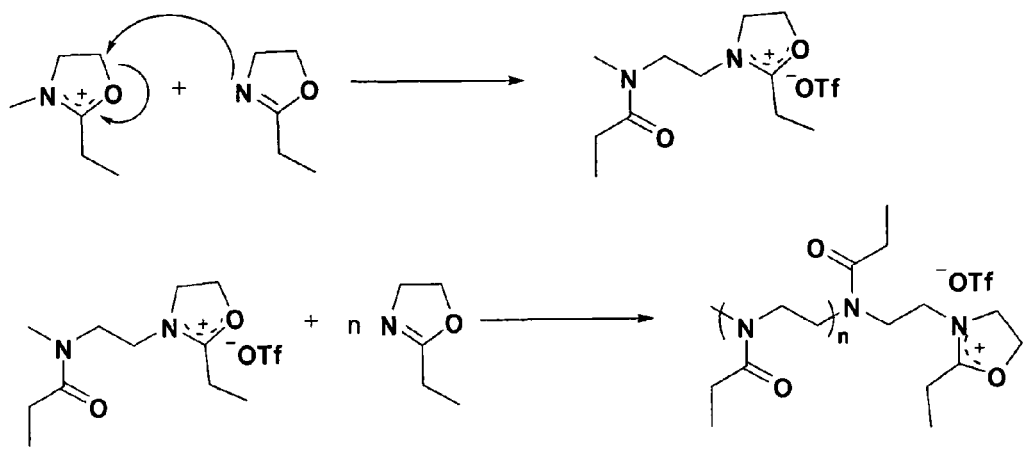
Termination
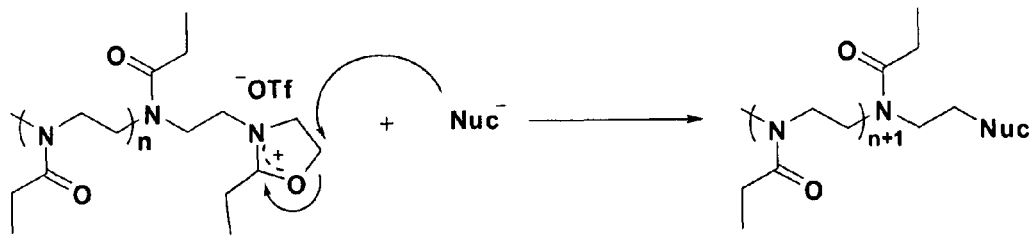
Figure 1. Living-cation mechanism for 2-alkyl-2-oxazoline (i.e. 2-ethyl-2-oxazoline) polymerization where $-OTf$ is $-OSO_2-CF_3$ or "triflate" and $Nuc^-$ is a negative nucleophile.

Figures 2A and 2B show gel Permeation chromatogram for M-PEOZ-OH 2000 prepared by the methods of the prior art.

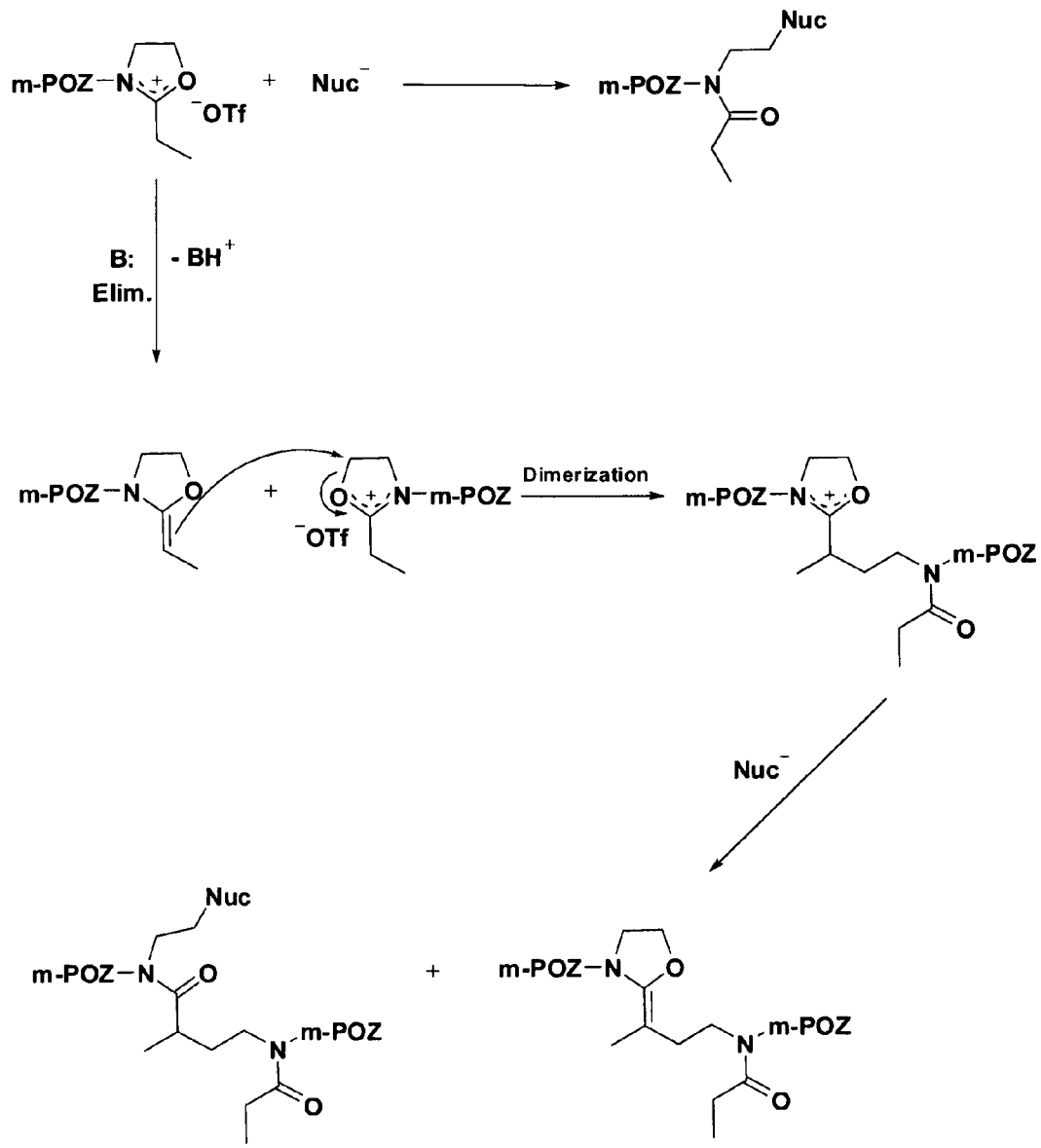
Figure 3. Elimination-dimerization mechanism for chain transfer during polymerization of 2-ethyl-2-oxazoline.

Figures 4A and 4B show gel permeation chromatogram for M-PEOZ-OH 2000 (Figure 4A) and M-PEOZ-OH 5000 (Figure 4B) prepared by optimized condition of current invention.

US 7,943,141 B2

ACTIVATED POLYOXAZOLINES AND COMPOSITIONS COMPRISING THE SAME

The present application claims the benefit of U.S. Provisional Application No. 60/892,212, filed Feb. 28, 2007.

FIELD OF THE DISCLOSURE

The present disclosure relates to polyoxazoline derivatives, methods of synthesis and intermediate compounds useful in producing such polyoxazoline derivatives, and hydrolytically stable target molecule-polyoxazoline conjugates produced using such polyoxazoline derivatives.

BACKGROUND

Polymer-modified therapeutics have proven to be of great utility in modern pharmaceutical science. In particular, proteins coupled to polyethylene glycols (PEGs) now constitute a number of therapeutics of great importance for treatment of a range of diseases. Due to the success of polymer-modified therapeutics, it is of interest to expand the range of polymers having such applications, especially to provide polymers having properties not possessed by polyethylene glycol.

BRIEF DESCRIPTION OF THE FIGURES

FIG. 1 illustrates the living-cation mechanism for 2-alkyl-2-oxazoline (e.g., 2-ethyl-2-oxazoline) polymerization where —OTf is —OSO$_2$—CF$_3$ or "triflate" and Nuc$^-$ is a negative nucleophile.

FIG. 3 shows a mechanism for the elimination-dimerization mechanism for chain transfer during polymerization of polyoxazoline derivatives, illustrated here as 2-ethyl-2-oxazoline.

DETAILED DESCRIPTION

Definitions

Figure 2A:
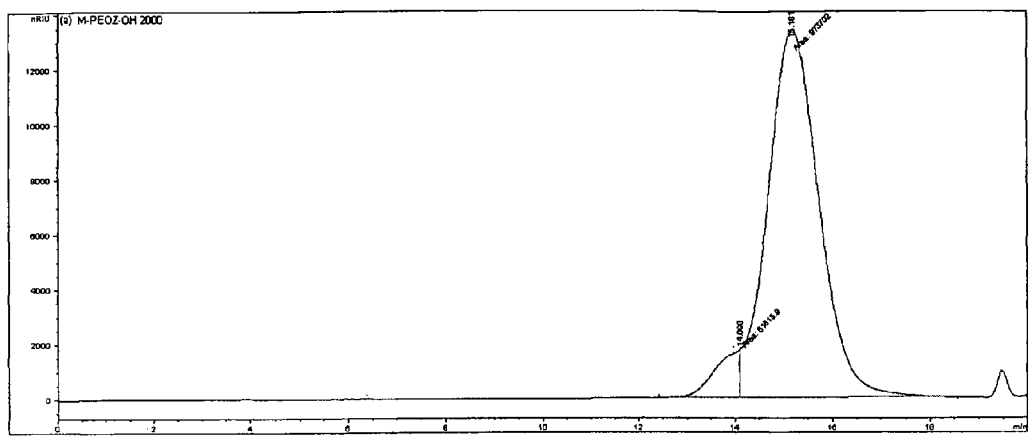
FIGS. 2A and 2B show gel permeation chromatogram for M-PEOZ-OH 2000 prepared by the methods of the prior art.

As used herein, the term "POZ", "POZ compound" or "POZ polymer" refers to a polymer of 2-substituted-2-oxazoline containing a repeating unit having the structure —[N(COR$_7$)CH$_2$CH$_2$]$_n$— in which R$_7$ is independently selected for each repeating unit from an unsubstituted or substituted alkyl, alkenyl, aralkyl or heterocyclylalkyl group and n is from 3-1000; in one embodiment, the unsubstituted or substituted alkyl, alkenyl, aralkyl or heterocyclylalkyl groups comprise from 1-10 carbon atoms, in a further specific embodiment, R$_7$ is methyl, ethyl or n-propyl.

As used herein, the term "PMOZ" refers to POZ with the repeating unit having the structure —[N(COCH$_3$)CH$_2$CH$_2$]$_n$—.

As used herein, the term "PEOZ" refers to POZ with the repeating unit having the structure —[N(COCH$_2$CH$_3$)CH$_2$CH$_2$]$_n$—.

As used herein, the term M-POZ, M-PMOZ or M-PEOZ refers to the polymers above in which the nitrogen on the initiating end is bound to methyl.

As used herein, the term "POZ derivative" or "polyoxazoline derivative" refers to a structure comprising a POZ polymer, the POZ polymer having a single active functional group on the terminal end of the POZ polymer, the functional group capable of forming a linkage, directly or indirectly, with a chemical group on a target molecule; in one embodiment the POZ derivative is a monofunctional POZ derivative.

As used herein, the term "target molecule" refers to any molecule having therapeutic, diagnostic application or a targeting function, wherein the target molecule is capable of reacting with an active functional group on a POZ polymer or a POZ derivative of the present disclosure, including, but not limited to, a therapeutic moiety (such as but not limited to a drug), a diagnostic moiety, a targeting moiety, an organic small molecule, an oligonucleotide, a polypeptide, an antibody, an antibody fragment and a protein.

As used herein, the term "hydrolytically stable target molecule-POZ conjugate" refers to a conjugate of a POZ derivative of the present disclosure and a target molecule, such that all the chemical linkages between the POZ conjugate and the target molecule are hydrolytically stable.

As used herein, the term "hydrolytically stable" refers to a linkage that is stable in aqueous solutions under physiological conditions; in one embodiment, such linkages are stable for at least 12 hours, 24 hours, 48 hours, 96 hours, 192 hours or greater; in an alternate embodiment such linkages are stable indefinitely.

As used herein, the term "hydrolytically unstable" refers to a linkage that is not stable in aqueous solutions under physiological conditions.

As used herein, the term "physiological conditions" refers to an aqueous solution having a pH from 6-8 and a temperature from 30-42 degrees Celsius.

As used herein, the term "active functional group" refers to those groups that react readily with electrophilic or nucleophilic groups or that react readily by cycloaddition reactions, in contrast to those groups that require strong catalysis, high temperatures or impractical reaction conditions in order to react.

As used herein, the term "link", "linked" "linkage" or "linker" when used with respect to a POZ derivative described herein, or components thereof, refers to groups or bonds that normally are formed as the result of a chemical reaction and typically are covalent linkages.

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thio-ethers such as S-benzyl thioether, and S-4-picolyl thioether; substituted S-methyl derivatives such as hemithio, dithio and aminothio acetals; and others.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl" and "unsubstituted alkynyl" refers to alkyl, alkenyl and alkynyl groups that do not contain heteroatoms.

The phrase "substituted alkyl", "substituted alkenyl" and "unsubstituted alkynyl" refers to alkyl alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl or alkenyl, group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl (CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocyclylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclyl alkyl group.

As used herein, the term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

General Description

Polyoxazolines (POZ) are polymers prepared from 2-substituted-2-oxazoline monomers. These polymers are water soluble and have been reported to be nontoxic in mammalian model systems. POZ is generally prepared by reaction of the appropriate stoichiometric amount of 2-alkyl-2-oxazoline with an electrophilic initiator, such as methyl p-toluenesulfonate (or "tosylate", $CH_3$—$OSO_2$—$C_6H_4$—$CH_3$) or methyl triflate ($CH_3$—$OSO_2$—$CF_3$), followed by termination with a nucleophile such as hydroxide or an amine. The polymer produced is conveniently described in shorthand with the initiating group designated by the leftmost group and the terminating group designated by the rightmost group, with the 2-alkyl-2-oxazoline component in the middle. Therefore, when this shorthand description is used in the current specification, it is intended that the left side of the designation presents the "initiator end" and the right side of the designation presents the "terminal end", unless designated otherwise.

For example, when the 2-substituted-2-oxazoline is 2-methyl-2-oxazoline, methyl tosylate is used as the initiator and hydroxide is used as the terminator, the following polymer is produced:

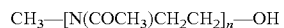

$$CH_3—[N(COCH_3)CH_2CH_2]_n—OH$$

The polymer above is conveniently described in shorthand notation as M-PMOZ-OH, in which the methyl initiator is designated by the leftmost M (at the initiator end), PMOZ represents polymethyloxazoline with the methyl of the repeating unit designated by the M of PMOZ, and the terminating hydroxyl is designated by the —OH (at the terminal end). The degree of polymerization, n, can range from approximately 3 to about 1000.

Another commonly used monomer is 2-ethyl-2-oxazoline, which with methyl triflate initiation and hydroxide termination would provide the following POZ polymer:

$$CH_3—[N(COCH_2CH_3)CH_2CH_2]_n—OH$$

The polymer above is conveniently described in shorthand notation as M-PEOZ-OH, in which the methyl initiator is designated by the leftmost M (at the initiator end), PEOZ represents polymethyloxazoline with the ethyl of the repeating unit designated by the E of PEOZ, and the terminating hydroxyl is designated by the —OH (at the terminal end).

More complex electrophiles and nucleophiles can be used. For example, initiation of 2-ethyl-2-oxazoline polymerization with benzyl bromide and termination with excess ethylene diamine yields the following polymer:

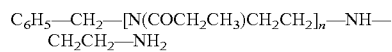

$$C_6H_5—CH_2—[N(COCH_2CH_3)CH_2CH_2]_n—NH—CH_2CH_2—NH_2$$

Also, different monomers can be used in the same polymer to yield various random and block copolymers.

The polymerization process is referred to as a living, cationic polymerization since initiation with an electrophile produces an oxazolinium cation that then reacts in a chain reaction with additional monomer units to produce a growing, "living" cation.

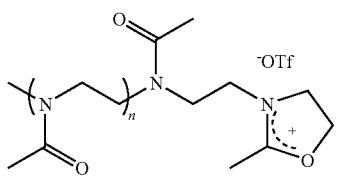

One can predict the products of termination by assuming that the living cation can be represented in the following non-cyclic form, although in reality the cyclic form is certainly the most important, and the desired products are produced by nucleophilic attack on the 5-position of the ring:

$$CH_3-[N(COCH_3)CH_2CH_2]_n-N(COCH_3)CH_2CH_2^+$$

In the current disclosure this cation will be represented as M-PMOZ$^+$. As noted above, this POZ cation can be "terminated" by reacting with nucleophiles such as hydroxide or amines. Interestingly, termination with the weak nucleophile water does not give the desired product of 5-attack (the "thermodynamic" product) but rather gives attack in the 2-position (the "kinetic" product). This kinetic product is not stable and can rearrange to give an ester product or undergo reversal to cation (O. Nuyken, G. Maier, A. Gross, Macromol. Chem. Phys. 197, 83-85 (1996)).

Hydroxyl terminated polymers can be further modified to give desired derivatives. For example, Zalipsky reacted the terminal —OH with glutaric anhydride to give a POZ terminated with a glutarate group (M. C. Woodle, C. M. Engbers and S. Zalipsky, Bioconjugate Chem., 1994, 5, 493-496).

$$M\text{-}PMOZ\text{-}O_2C-CH_2CH_2CH_2-CO_2H$$

The above polymer was activated as the succinimidyl ester and coupled to phospholipids and used to prepared POZ-modified liposomes. These liposomes were found to have similar properties to PEG-modified liposomes.

Amine terminated polymers also provide useful reactive groups for further derivatization. For example, termination with methyl amine gives a POZ terminated with the active group —NHCH$_3$. Termination with the cyclic diamine piperazine can also be useful.

Oxazoline polymerizations can also be initiated with functional nucleophiles. For example, the electrophilic initiator ethyl 3-bromopropionate has been used to initiate 2-ethyl-2-oxazoline polymerization. Termination with hydroxide gives the following polymer:

$$HO_2C-CH_2CH_2-[N(COCH_2CH_3)CH_2CH_2]_n-OH$$

It is noteworthy that POZs having the same functional group on the initiator end and the terminal end are chemically different because the group at the initiator end is attached to nitrogen while the group at the terminal end is attached to carbon. For example, the following two polymers are both propionic acid derivatives of PMOZ but differ in that the propionic acid at the initiator end is attached to nitrogen and the propionic acid at the terminal end is attached to carbon (the beginning or ending monomer unit is shown for clarity):

$$HOOCCH_2CH_2-N(COCH_3)CH_2CH_2-PMOZ\text{-}OH$$

$$M\text{-}PMOZ\text{-}N(COCH_3)CH_2CH_2-O-CH_2CH_2COOH$$

Yet another route to preparing polyoxazolines with active functional groups is to copolymerize a monomer such as 2-ethyl-2-oxazoline with an oxazoline monomer having an active functional group in the 2-position. For example, Jordan and colleagues have prepared oxazolines with acetylenes and protected aldehydes, carboxylic acids and amines in the 2-position (F. C. Gaertner, R. Luxenhofer, B. Blechert, R. Jordan and M. Essler, J. Controlled Release, 2007, 119, 291-300). Copolymerization of these functional monomers with 2-ethyl-2-oxazoline gives random copolymers with multiple pendent or side-chain active functional groups. For example, initiation with methyl triflate of polymerization of 2-ethyl-2-oxazoline and 2-pentynyl-2-oxazoline, followed by termination with piperazine (NHC$_4$H$_8$NH) gives the following random copolymer:

$$CH_3-\{[N(COCH_2CH_3)CH_2CH_2]_n-[N(COCH_2CH_2-CCH)CH_2CH_2]_m\}_{ran}-NC_4H_8NH$$

The subscript "ran" indicates that the polymer is a random copolymer. Values of n are typically around 20-30 while m is around 2-5.

To couple a POZ to a target molecule, such as, but not limited to, a polypeptide, it is necessary to "activate" the polymer by attaching an active functional group to at least one terminus of the polymer that is capable of forming a linkage with a group on the target molecule. There has been little work done on activation of POZ for coupling to target molecules. The active group may be added at the initiator (left) end or terminal (right) end, or both. For example, when the target molecule is a polypeptide, the polypeptide has a number of amino groups on the surface that can react with the active functional group on the POZ, and in the only published example of attachment of POZ to a protein, Myamoto and colleagues attached the POZ below to amino groups of the enzyme catalase (M. Myamoto, T. Saegusa, et al., Macromolecules, 1990, 23, 3201-3205):

$$M\text{-}PMOZ\text{-}O_2C-CH_2CH_2CH_2-CO_2-NHS$$

In this case M-PMOZ-OH was reacted with glutaric anhydride, and the resulting carboxylic acid was activated with N-hydroxysuccinimide, which is represented as NHS. NHS active esters are commonly used active forms of carboxylic acids. In this example the POZ-catalase conjugate proved to be active.

The prior art has described three terminally-activated POZ compounds capable of being conjugated to a target molecule. However, each of the previously described POZ derivatives suffers from limitations. Zalipsky described an activated propionic acid POZ compound, NHS—OOCCH$_2$CH$_2$—PEOZ-OH where the activating group was attached to the initiator end of the molecule (S. Zalipsky, C. B. Hansen, J. M. Oaks and T. M. Allen, J. Pharm. Sci., 85, 133-137 (1996)). The POZ compound was made by initiation of polymerization using a moiety containing the activating group. However, Jordan, Hoogenboom and others have shown that initiation of polymerization with different activating groups can require greatly differing reaction conditions requiring extensive studies to determine optimal reaction conditions. Thus if one chooses the initiator method to make activated POZ compounds, one must conduct exploratory work to determine appropriate reaction conditions for each new compound. Also the above compound is difunctional since it is terminated with a hydroxyl group rather than an inert group such as an alkyl group. Also, as discussed below, initiation of polymerization with an alkyl halide does not proceed by a living-cation mechanism and thus high polydispersities are found.

The NHS-activated glutarate derivative has been made by Myamoto and Zalipsky. This derivative was prepared from a monofunctional POZ polymer having an OH group as the terminal activating group (M-PMOZ-OH). However, glutarate and succinate derivatives have a hydrolytically unstable ester linkage connecting the target molecule to the POZ compound. For example, the NHS-activated glutarate derivative will react with a target molecule, illustrated here as a protein, as shown:

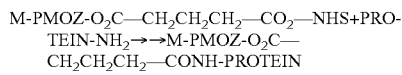
M-PMOZ-O₂C—CH₂CH₂CH₂—CO₂—NHS+PRO-
TEIN-NH₂→→M-PMOZ-O₂C—
CH₂CH₂CH₂—CONH-PROTEIN As a result of the hydrolytically unstable ester linkage, the target molecule-POZ conjugate produced will not be stable in a biological system under physiological conditions, such as a human or other mammal, but will hydrolyze to cleave the POZ from the protein:

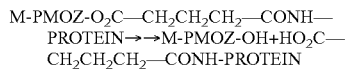
M-PMOZ-O₂C—CH₂CH₂CH₂—CONH—
PROTEIN→→M-PMOZ-OH+HO₂C—
CH₂CH₂CH₂—CONH-PROTEIN Furthermore, in the scheme above, when the target molecule-POZ conjugate undergoes hydrolysis due to the cleavage of the unstable ester linkage, the resulting target molecule will contain a "tag" or "hapten" which can lead to immunogenicity of the target molecule.

Finally, the orthopyridyl disulfide (OPSS) derivative has been made (G. Hsiue, et al., Bioconjugate Chem., 2006, 17, 781-786). This derivative could in theory be coupled to a protein thiol group to give a disulfide linkage, although this was not done by Hsiue, but it is known that disulfides are unstable and subject to ready reduction in plasma.

An additional problem hindering use of known POZ polymers for modification of target molecules is that some POZ polymers do not possess a single active functional group; i.e., they are not "monofunctional". Monofunctionality is necessary if one seeks to avoid crosslinking and or incorporation of multiple target molecules on the polymer backbone. For example, Jordan and his colleagues have published work showing copolymerization of 2-ethyl-2-oxazoline with oxazoline monomers containing functional groups. These pendent functional groups are capable in some instances of being coupled to peptides. However, this technique was not designed to provide monofunctional POZ polymers but rather produces multifunctional compounds with pendent groups along the backbone. Having multiple functional groups present in the POZ backbone can be advantageous in some instances, but would lead to crosslinking and aggregate formation when coupling with multi-functional target molecules, such as, but not limited to, polypeptides and proteins. Also there are instances when one would desire to have a single target molecule coupled to a polymer, and multi-functional POZ polymers will not permit this.

Some of the above functional POZ compounds have the potential to be coupled to target molecules such as proteins and small molecule drugs. However, as work with polyethylene glycol-modified therapeutics has shown, it is frequently necessary for commercial development of polymer-modified drugs to utilize polymers with molecular weights (MWs) as high as 40,000 Da or higher and with molecular weight distributions or polydispersities (PDs) of less than 1.1. There has been a great deal of work showing that MWs and PDs in the above range cannot be achieved for POZ with conventional techniques. It is generally seen that as the molecular weight of growing POZ chains reaches approximately 5,000 Da, the polydispersity increases appreciably. Side reactions, including chain transfer, begin to grow in importance. Use of unusually low polymerization temperatures combined with reaction times of several weeks has been shown to give acceptable PDs, but such conditions are not practical for commercial-scale preparations (J. S. Park and K. Kataoka, Macromolecules, 39, 6622 (2006)). Hoogenboom, Schubert and colleagues indicate that low-PD POZ can be prepared by using microwave irradiation, but again commercial-scale polymerizations are not available with this technique (R. M. Paulus, T. Erdmenger, C. R. Becer, R. Hoogenboom and U.S. Schubert, Macromol. Rapid Comm., 28, 484-491 (2007)). As a consequence of the generally found broad polydispersities, the functional POZ compounds described to date are seriously limited for use in polymer therapeutics.

Yet another problem hindering use of POZ derivatives in modification of target molecules is the unavailability of a range of appropriate activated POZ molecules capable of reaction with the target molecules under a range of conditions. Furthermore, the POZ molecules presently available are multifunctional or contain hydrolytically unstable bonds when conjugated to target molecules, with the disadvantages associated therewith, or the active substituent is added during the initiation reaction, with the disadvantages associated therewith. Furthermore, pendent functionality has been described, but these derivatives are multifunctional and not suitable for the current application.

SUMMARY OF THE INVENTION

The present disclosure provides monofunctional POZ derivatives having a range of active groups allowing conjugation of the monofunctional POZ derivatives to a wide range of target molecules under a wide range of reaction conditions to produce a hydrolytically stable target molecule-POZ conjugate in which one target molecule is bound to the POZ derivative. The ability to provide monofunctional POZ derivatives with a range of active groups capable of reacting with a selected group on a target molecule under different reaction conditions provides a significant advantage over the prior art since different target molecules are sensitive to different reaction conditions and the most effective reaction conditions for conjugation of a POZ derivative to a target molecule frequently vary depending on the nature of the target molecule and the group on the target molecule reacting with the POZ derivative.

The present disclosure addresses the limitations of the previously described POZ polymers by providing a range of POZ derivatives not previously known in the art. In addition, the present disclosure provides monofunctional POZ derivatives not previously known in the art. Furthermore, the present disclosure provides monofunctional POZ derivatives having active functional groups on the terminal end thereof. Still further, the present disclosure addresses the limitations of the prior art by providing synthesis methods for the disclosed POZ derivatives utilizing POZ molecules with terminator end groups, such as, but not limited to, the hydroxyl group, that are readily available and can be obtained using known preparation chemistries. A wide variety of POZ derivatives can then be prepared by coupling of small, active molecules to the available terminal group in a step-wise fashion to generate the desired active functional groups on the POZ derivative (as described herein). In addition, the present disclosure addresses the limitations of the prior art by providing a hydrolytically stable target molecule-POZ conjugate through the use of the described monofunctional POZ derivatives. Such an approach not only provides a target molecule-POZ conjugate in which not more than one target molecule is bound to each POZ derivative, but also increases the in vivo half-life of the target molecule-POZ conjugate and reduces the problems of immunogenicity related to "hapten tagging" of the target molecule. The disclosed monofunctional POZ derivatives, synthesis methods and resulting hydrolytically stable target molecule-POZ conjugates have not been appreciated in the art.

Therefore, the described monofunctional POZ derivatives and synthesis methods avoid the problems inherent in the art and provide a mechanism to produce hydrolytically stable target molecule-POZ conjugates in which one target molecule is bound to the POZ derivative.

Any 2-substituted-2-oxazoline compound, such as but not limited to, PMOZ and PEOZ, may be used to produce the POZ derivatives of the present disclosure, as discussed in more detail below. In certain embodiments, PEOZ or PMOZ are the 2-substituted-2-oxazolines POZ molecules. As is known in the art, different alkyl groups in the 2-alkyl-2-oxazoline molecules can provide differing solubilities, pharmacokinetics and membrane permeating abilities to the POZ derivatives described herein. In addition, the nature of the repeating unit in the POZ polymer backbone may be the same to produce a homopolymer (such as but not limited to PMOZ and PEOZ) or at least one of the repeating units may be different to provide for copolymers, such as, but not limited to, random or block copolymers.

Furthermore, the present disclosure provides novel methods for synthesizing POZ polymers with low polydispersity (PD) values and decreased amounts of impurities produced by unwanted side reactions, such as, but not limited to, chain transfer. In one embodiment, the present disclosure describes novel methods for minimizing unwanted side reactions, such as, but not limited to, chain transfer, allowing the production of POZ polymers of increased purity with low PD values. In one embodiment, the methods of the present disclosure provide for POZ derivatives with low PD values at increased MW values. In a further embodiment, POZ polymers are produced with decreased amounts of impurities. The novel methods provided for in the present disclosure are an improvement over the methods of the prior art and provide for large scale commercial preparation of POZ polymers suitable for use in modification of a wide variety of target molecules.

Therefore, the present disclosure also provides POZ polymers of increased purity and with low PD values suitable for use in pharmaceutical applications. As is known in the art, PD values will vary with MW; in general, as the molecular weight increases the PD value also increases. Using the methods of the present disclosure, POZ polymers of various MWs can be produced on commercial scale with lower PD values at a given MW than can be produced using the commercially-applicable methods of the prior art. For example, using the methods of the present disclosure, POZ derivatives of 20,000 Da MW or less can be produced with PD values of less than or equal to 1.1. In a further particular embodiment, the foregoing are produced with decreased amount of impurities. As is known in the art and illustrated in the Examples herein, POZ derivatives synthesized using the methods of the prior art exhibit certain impurities that are seen as high MW shoulders and low MW tails in GPC traces. These impurities are generated, at least in part, through unwanted side reactions, such as, but not limited to, chain transfer. As a result, the disclosed POZ derivatives are suitable for use in modification of a wide variety of target molecules.

Through the use of the methods described herein, a range of monofunctional POZ derivatives with different active functional groups are provided. Furthermore, the present disclosure provides synthesis methods to produce such monofunctional POZ derivatives in an efficient manner. Finally, through the use of the monofunctional POZ derivatives described, a hydrolytically stable target molecule-POZ conjugate may be produced in which one target molecule is bound to the POZ derivative.

Methods of Synthesis of POZ Derivatives with Low PD Values

The current state of the art for polymerization of 2-aryl- and 2-alkyl-2-oxazolines is derived from the publications of Kobayshi, Nuyken and Jordan (S. Kobayashi, E. Masuda, S. Shoda and Y. Shimano, Macromolecules, 1989, 22, 2878-2884; A. Gross, G. Maier and O. Nuyken, Macromol. Chem. Phys., 1996, 197, 2811-2826; and F. C. Gaertner, R. Luxenhofer, B. Blechert, R. Jordan and M. Essler, J. Controlled Release, 2007, 119, 291-300). In these methods polymerization is initiated with an electrophile, such as an alkyl tosylate or alky triflate; in one embodiment, methyl tosylate or methyl triflate is used. These strong electrophiles are used to favor polymerization by a living-cation mechanism since this mechanism, in theory, gives no termination or chain-transfer reactions (Q. Liu, M. Konas and J. S. Riffle, Macromolecules, 1993, 26, 5572-5576) (see FIG. 1). However, it is known from the prior art that chain transfer reactions do occur and that the reaction does not proceed strictly by the living cation mechanism. If weak electrophiles such as, but not limited to, alkyl halides are used, the reaction proceeds by a covalent mechanism with a consequent significant increase in PD. The prior art polymerization methods utilize chlorobenzene, dichlorobenzene or acetonitrile as solvent. The propagation phase is conducted at approximately 80° C. for approximately 1-3 days. Termination is conducted by heating at 80-90° C. with aqueous sodium carbonate to give a hydroxyl terminal group or by reacting with a secondary amine such as morpholine or piperidine to give a terminal tertiary amine.

The use of these typical, prior art methods leads to the presence of a high-MW shoulder of approximately 5-10% and significant low-MW tailing in gel permeation chromatography. Such results have been noted in the art (see J. Park and K. Kataoka, Macromolecules, 2006, 39, 6622-6630.). It is generally stated in the literature that this broadening of the MW distribution is due to chain transfer proceeding through an elimination-dimerization mechanism, although structural details and experimental support for this process are limited (M. Litt, A. Levy and J. Herz, J. Macromol. Sci.-Chem., 1975, A9, 703-727). To the extent that chain transfer reactions do occur, such reactions cannot be considered to be truly living polymerizations. Therefore, it would be beneficial to reduce the occurrence of unwanted side reactions such as chain transfer.

The applicants have clarified the details of the elimination-dimerization mechanism, provided experimental support for the mechanism, and proposed implications of the mechanism regarding the termination step. This latter advance is particularly important because it shows why certain termination reactions fail and it leads us to choose termination reactions that succeed. Such a finding has not been described in the art and it provides guidance in creating synthetic methods that minimize the occurrence of unwanted side reactions and that yield the desired terminated products.

As discussed herein, the use of the prior art methods produced a POZ product that contained a high MW shoulder of approximately 5-10% of the total mass of the POZ product. This high MW shoulder contributes to the unacceptable PD values obtained using synthetic methods of the prior art. The high MW shoulder observed in the methods of the prior art is composed, at least in part, of a high-MW dimer that is formed during the polymerization and/or termination steps (see FIG. 3). The elimination-dimerization mechanism predicts that if chain transfer occurs during the termination step, the material in the high MW shoulder would be approximately double the MW of the desired product. Furthermore, if chain transfer occurs during the propagation step, a new polymer chain will be initiated, and since monomer concentration is less at this point, the MW of this polymer will be less than that of the bulk of polymer. In addition, since this new polymer chain results from chain transfer, it must be initiated by a proton, rather than by methyl, and thus the MALDI spectrum of this polymer will show a set of peaks 14 Da less than that of the main peak.

There are implications regarding the termination step as well, which have not been appreciated to date. For example, the addition of a terminating nucleophile which is a strong base and weak nucleophile is predicted to result in significant elimination and dimerization. Furthermore, the oxazolinium cation is a delocalized or "soft" electrophile, and theory predicts that a "soft" or diffuse nucleophile would be more likely to act as a terminating nucleophile than as a base. As an example, one would expect a "soft" mercaptide to be a more effective terminating agent than a "hard" alkoxide.

The above predictions were confirmed experimentally. In one example, sterically hindered ethyldiisopropylamine (a strong base and weak nucleophile) was added to terminate 2-ethyl-2-oxazoline polymerization. This reaction resulted in an increase of high MW dimer product to 75% (see Example 3). It was confirmed that the MW of the impurity peak in GPC is approximately double that of the MW of the desired product. In addition, the MALDI-TOF spectrum confirmed that a portion of the main peak exhibited a second set of peaks that are 14 mass units less than expected. We have observed that the MW of this second set of peaks is somewhat less than twice that of the desired product. Presumably this occurs because some chain transfer takes place during the propagation phase before polymer is fully formed and monomer is depleted; in this case the base must be monomer since it is the strongest base present during propagation.

In addition, termination by alkoxides, which are known as hard nucleophiles, leads to significant amounts of high MW dimer with no product derived from the desired nucleophilic attack (see Example 5). In addition, termination by mercaptides, which are known as soft nucleophiles, does, as predicted, lead to the desired product of nucleophilic attack (see Example 11).

As a result of the foregoing observations, the applicants have developed novel synthetic methods that reduce unwanted side reactions, such as chain transfer, and allow the production of POZ polymers and derivatives with superior properties as compared to the prior art. The improved methods may utilize one or more of the following improvements.

In one embodiment, the POZ polymerization reaction is initiated with a strong electrophile such as, but not limited to, alkyl tosylate or alkyl triflate; in one embodiment, methyl tosylate or methyl triflate are used.

The elimination-dimerization mechanism also suggests that both propagation and termination should be conducted at low temperature since bimolecular eliminations are favored by high temperatures. The Examples confirm this observation by showing that high MW dimer formation is reduced by lowering temperature of both propagation and termination. This prediction has also been confirmed by Kataoka (see J. Park and K. Kataoka, Macromolecules, 2006, 39, 6622-6630). However, if one lowers the temperature sufficiently to eliminate all chain transfer it can take weeks to reach completion of the reaction, and thus such reactions are not commercially viable. The present disclosure describes methods below which are commercially viable. We have observed that continuing heating after propagation is complete or nearly complete will cause a buildup in elimination-dimerization. The present disclosure has surprisingly found that POZ derivative quality is greatly improved by terminating the polymerizations much earlier and at lower temperatures than in the state-of-the-art methods. In addition, the duration of the propagation reaction is the minimum time required for complete or substantially complete (greater than or equal to 90%) monomer consumption. It should be noted that the temperature and the duration of the propagation reaction are interrelated. In other words, higher propagation temperatures may be used with shorter propagation reaction times. Conversely, if longer propagation reaction times are used, the temperature should be reduced accordingly.

It has also been found that the use of solvents, such as but not limited to, chlorobenzene, provide faster polymerization than the commonly used acetonitrile solvent, which is critical for commercial, large scale preparations of POZ products. While the prior art has recognized chlorobenzene as solvent, the improvement in reaction rates has not been recognized. The unexpected result that using chlorobenzene as a solvent provides faster reaction times allows the polymerization reaction to be terminated earlier and at higher temperatures without increasing the formation of high MW dimer products. Such an improvement was not appreciated in the art.

Furthermore, filtration of POZ products, especially those terminated with OH groups, through cation-exchange resins improves PD values. It is believed that such filtration removes low-MW and high-MW products. The effect of filtration is especially significant for higher molecular weight POZ products (for example, those products of 10,000 Da and above); however, filtration provides benefits for POZ derivatives regardless of MW. To give one example of this improvement, unfiltered M-PEOZ-OH 10,000 (produced by the methods of the present disclosure) showed Mn 7950 Da and PD 1.21 (GPC), with a significant low-MW tail. Filtration of this product through carboxyethyl-Sepharose gave Mn 9180 Da and PD 1.05 (from GPC) and Mn 9780 and PD 1.01 (from MALDI), with no observable low-MW tailing and a slight 2% high-MW shoulder (as determined by GPC). The fact that the high-MW shoulder was not revealed for the crude product shows that the cation-exchange filtration removed high-MW as well as low-MW impurities.

Furthermore, in certain cases if the POZ product comprises a carboxylic acid as the terminal group, anion-exchange chromatography can be used to isolate the desired product and remove any high molecular weight products that are formed. We have conducted this experiment for M-PEOZ-S—$CH_2CH_2$—$CO_2H$. It is noteworthy that this chromatography experiment showed that the high-MW dimer was neutral. Hence the major dimerization product must be the alkene of FIG. 3. In this experiment, the crude product had Mn of 9600 Da, PD of 1.09 (GPC) and 6% high-MW shoulder. After anion-exchange chromatography on DEAE-Sepharose, Mn was 9500 Da, PD was 1.06 (GPC), and there was no high-MW shoulder.

In an additional embodiment, the termination reaction is conducted at a low temperature (in one embodiment, less than 80° C.; in an alternate embodiment from 15 to 40° C.) and with a nucleophile which is a better nucleophile than it is a base; exemplary nucleophiles include, but are not limited to, soft nucleophiles such as mercaptides. The applicants have found that the use of sodium alkoxide compounds as terminating agents does not produce the desired products; rather, the unterminated cation remains. However, the use of sodium mercaptides and related compounds, such as, but not limited to, NaS—$CH_2CH_2$—$CO_2Et$, give effective termination and yields POZ products with desired properties, such as but not limited to, low PD values. Hydrolysis of this ester to the carboxylic acid, followed by anion-exchange chromatography, gives high quality POZ product with low PD values and with no high-MW shoulder. In one such example M-PEOZ-S—CH$_2$CH$_2$—CO$_2$H of Mn 9600 Da, PD of 1.09 (GPC), and 6% shoulder was produced. Anion-exchange chromatography on DEAE-Sepharose gave Mn 9500, PD 1.06 (GPC) and no shoulder.

These novel improvements in synthesis are utilized in the preparation of the POZ polymers and derivatives described herein. As would be obvious to one of ordinary skill in the art, the improvements in synthesis may be used in various combinations; the foregoing should not be interpreted as requiring each of the improvements to be used in a given synthesis.

The methods of the prior art were used to synthesize M-PEOZ-OH 2000 by two methods. The description of the synthesis of these POZ derivatives is provided in Example 1 (for FIG. 2A) and Example 2 (for FIG. 2B). The produced POZ derivatives were analyzed. For the POZ derivative of FIG. 2A, GPC showed a single peak with an appreciable high-MW shoulder (Mn=3600 Da, 9%). The main peak had a Mn of 1980 Da, PD 1.08. NMR showed the expected peaks (see Example 6). MALDI-TOF MS gave a set of peaks with a maximum at 2000 Da, PD 1.04 and 99.1 Da separation. The MALDI spectrum also showed a second set of peaks with 99.1 Da separation, but with each peak 14 Da less than the main set. The maximum for this set of peaks occurred at 1600 Da. For the POZ derivative of FIG. 2B, GPC showed a single peak with an appreciable high-MW shoulder (Mn=3300 Da, 6%). The main peak had a Mn of 2200 Da, PD 1.06. NMR showed the expected peaks (see Example 6). MALDI-TOF MS gave a set of peaks with a maximum at 2300 Da, and 99.1 Da separation. The MALDI spectrum also showed a second set of peaks with 99.1 Da separation, but with each peak 14 Da less than the main set. The maximum for this set of peaks occurred at 2100 Da.

Figure 4A:
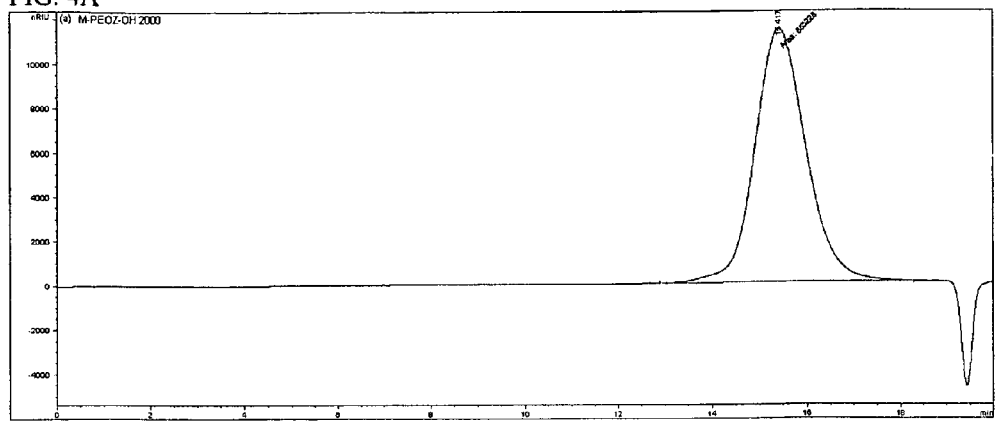
FIGS. 4A and 4B shows gel permeation chromatogram for M-PEOZ-OH 2000 (FIG. 4A) and M-PEOZ-OH 5000 (FIG. 4B) prepared by optimized conditions of the current invention.
Figure 4B:
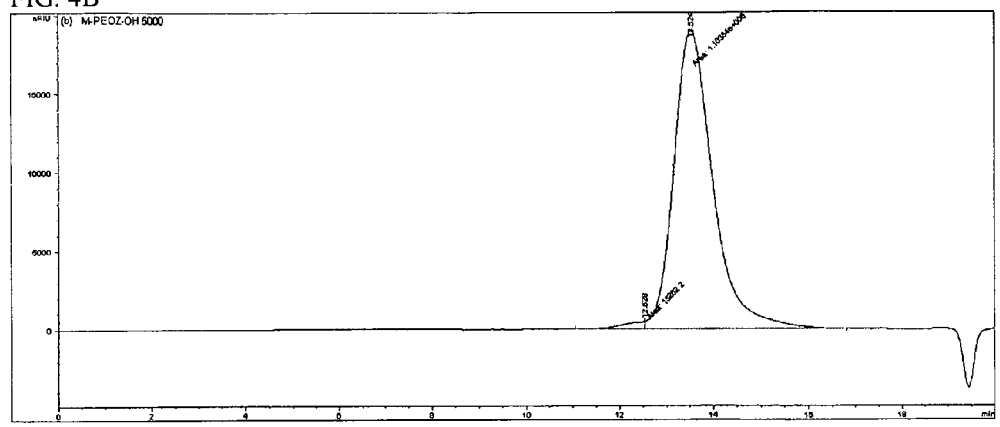

The methods of the present disclosure were used to synthesize two POZ derivatives, M-PEOZ-OH 2000 (FIG. 4A) and M-PEOZ-OH 5000 (FIG. 4B) for comparison. The description of the synthesis of these POZ derivatives is provided in Example 6 (for FIG. 3A) and Example 7 (for FIG. 4B). The GPC chromatograms are provided in FIGS. 4A and 4B. FIGS. 4A and 4B show the greatly improved GPCs of M-PEOZ-OH 2000 and 5000 obtained using the synthesis methods of the present disclosure. For M-PEOZ 2000 the reaction conditions were: (a) methyl triflate initiation, propagation in chlorobenzene at 110° C. for 1.5 hours, and termination at room temperature with aqueous carbonate. The M-PEOZ 2000 derivative was observed to have a Mn of 1900 Da (from MALDI and GPC), a PD of 1.07 (GPC) and 1.03 (MALDI) and no high-MW shoulder and no low-MW tail. For M-PEOZ-OH 5000 the reaction conditions were: (a) methyl triflate initiation, propagation in chlorobenzene at 42° C. for 1 hour and then 80° C. for 3.75 hours, and termination at room temperature with aqueous carbonate. The M-PEOZ 5000 derivative was observed to have a Mn of 4900 Da (from MALDI), a PD of 1.06 (GPC) and 1.02 (MALDI), a very slight high-MW shoulder (1%) and no low-MW tail. M-PEOZ-OH 10,000 prepared under similar conditions gave Mn of 9780 Da (MALDI), PD of 1.01 (MALDI) and 1.05 (GPC), and a very slight high-MW shoulder of 2%.

In summary, the applicants of the present disclosure have identified the nature of the unwanted side reactions that occur when using the synthesis methods of the prior art thereby allowing the applicants to identify reaction conditions that minimize the contribution of such side reactions. As a result, the methods of the present disclosure allow for the preparation of POZ polymers and derivatives with superior properties over those available in the art. In one embodiment, the methods of the present disclosure allow for the preparation of POZ polymers and derivatives with low PD values; in a particular embodiment, the methods of the present disclosure allow for the preparation of POZ polymers and derivatives with low PD values at high MW values. In addition, the methods of the present disclosure allow the production of the foregoing in a manner suitable for large scale production. Such POZ polymers and derivatives with such characteristics, as well as methods for producing the same have been lacking in the art.

In one embodiment, the methods of the present disclosure provide such benefits in POZ polymer synthesis by providing a reduction, either completely or partially, of one or more side reactions that occur during the initiation, polymerization or termination processes of POZ synthesis. In a particular embodiment, the side reaction is the chain transfer process. Such unwanted side reactions, such as, but not limited to, the chain transfer process, are a problem in current state of the art procedures for manufacturing POZ products. Such side reactions provide POZ derivatives with unwanted characteristics, such as high PD values.

Methods of Synthesis of Monofunctional POZ Derivatives

The present disclosure provides novel methods to synthesize the described monofunctional POZ derivatives. The novel synthetic methods are referred to herein generally as the building block method. In one embodiment of the building block method, a one-step synthetic method is disclosed. In an alternate embodiment of the building block method, a two-step method is disclosed. In a further alternate embodiment of the building block method, a living polymer synthesis is described. Each of the methods will be described in more detail below.

Building Block One-Step Method

In a first embodiment of the building block approach, a one-step method is disclosed. In the one-step method, a range of monofunctional POZ derivatives is generated in a single step through reaction between a single terminally-functionalized POZ molecule and a set of compounds containing the desired active group. In this way a single terminally-functionalized POZ molecule can be converted to a range of activated monofunctional POZ derivatives. This approach means that one need only optimize the polymerization chemistry for production of a single monofunctional POZ derivative. The POZ terminal group (Y below) is chosen carefully to make possible this range of reactions to provide a range of active groups. The one-step method can be represented as follows in its general form in Scheme 1:

Scheme 1

I

Where

POZ is —[N(COR$_7$)CH$_2$CH$_2$]$_n$—;

R$_7$ is independently selected for each repeating unit from an unsubstituted or substituted alkyl, alkenyl or aralkyl group, in one embodiment having from 1 to 12 carbons;

R$_1$ is hydrogen or unsubstituted or substituted alkyl, alkenyl or aralkyl group groups;

R$_2$-R$_4$, R$_{11}$ and R$_{14}$-R$_{15}$ are each independently selected from hydrogen or unsubstituted or substituted alkyl, alkenyl or aralkyl group groups, in one embodiment having from 1 to 10 carbons;

R$_8$ is —C$_6$H$_{10}$—C$_2$— (cyclohexylmethylene);

R$_{23}$ is unsubstituted or substituted alkyl, alkenyl, alkynyl or aralkyl group groups, in one embodiment having from 1 to 10 carbon atoms, or substituted or unsubstituted aryl groups;

Y is —OH, —SH, —S—(CH$_2$)$_k$—CO$_2$H, piperazinyl, substituted piperazinyl, substituted piperidinyl, or —NHR$_2$;

P is a linking group; P can be any group capable of forming the linkages shown in scheme 1 and may be selected depending on the chemistry of the groups with which it forms a linkage; representative P groups include, but are not limited to, —O—, —S—, —NH—, —NR$_{11}$— or unsubstituted heterocyclyl, such as, but not limited to, piperazinyl (NC$_4$H$_8$N);

Q is a linking group; Q can be any group capable of forming the linkages shown in scheme 1 and may be selected depending on the chemistry of the groups with which it forms a linkage; representative Q groups include, but are not limited to, an unsubstituted or substituted alkyl, alkenyl, heterocyclyl or aryl group, —(CH$_2$)$_m$—CONH—(CH$_2$)$_m$—, —NH—(CH$_2$)$_m$—NHCO—(CH$_2$)$_m$, —CO—(CH$_2$)$_m$—, —CO—C$_6$H$_4$—, or —CO—R$_8$, —(R$_{15}$)$_m$— or —(CR$_3$R$_4$)$_m$—;

n is an integer from 3 to 1000;

k and m are integers independently selected from 1 to 10;

p and q are integers independently selected from zero or one;

X is an active functional group capable of forming a linkage with a target molecule to produce a hydrolytically stable target molecule-POZ conjugate.

In one embodiment, the active functional group is selected from the following general classes of compounds: aldehydes (—CHO), active carbonates (—O—CO—Z), maleimides, sulfonate esters (—OSO$_2$—R$_{23}$), including but not limited to tresylate (2,2,2-trifluoroethanesulfonate) and mesylate (—O—SO$_2$—CH$_3$ or —OMs), hydrazides (—CONHNH$_2$), epoxides, iodoacetamides, alkynes, azides (—N$_3$), isocyanates (—OCN), cyanates (—NCO), isothiocyanates (—SCN), thiocyanates (—NCS), nitriles (—CN), carbonyldiimidazole derivatives, vinylsulfones, carboxylic acid halides, active esters (—CO-Z) and carboxylic acids (—CO$_2$—H); and Z is an activating group of which there are many known in the art including N-succinimidyloxy, chlorine, bromine, sulfo-N-succinimidyloxy, p-nitrophenoxy, 1-imidazolyl, and 1-benzotriazolyloxy;

The active functional group may also be protected to yield a protected active functional group by methods known in the art. For example, an acetal [CH(OR$_{14}$)$_2$] is an exemplary protecting group, which can be hydrolyzed to produce an aldehyde group. The active functional group may be substituted with groups, such as but limited to, those groups described with respect to a substituted alkyl group and substituted and unsubstituted alkyl, alkenyl, alkynyl, aralkyl or heterocycloalkyl groups. Furthermore, the active functional group includes those compounds that may be converted to an active functional group. For example, the X group may include a compound that is modified by a linkage that is susceptible to hydrolysis under certain reaction conditions (such as those used to join the POZ derivative to a target molecule), thereby cleaving the linkage and exposing the active functional group to react with a group on the target molecule.

In Scheme 1, the reactant R$_1$-POZ-Y is the direct product of polymerization of POZ and the Y group is capable of being converted directly to a series of monofunctional POZ derivatives capable of forming a hydrolytically stable target molecule-POZ conjugate. For example, in one embodiment Y equals —OH and is obtained when the POZ polymerization reaction is terminated with hydroxide. In an alternate embodiment, Y equals —NHR$_2$ and is obtained when the POZ polymerization reaction is terminated with a compound containing an amino group, R$_2$NH$_2$. Other useful amine terminating agents providing useful Y groups are piperazine or a substituted piperazine such as 1-piperazinepropanol (H—NC$_4$H$_8$N—CH$_2$CH$_2$CH$_2$—OH) Substituted piperidines are also useful since these provide the rapid termination usual for amines, and they also introduce a range of functional groups. Commercially available substituted piperidines include 4-piperidine butyric acid, 3-piperidine carboxylic acid and 4-piperidine methanol. In an alternate embodiment, Y equals —S—CH$_2$CH$_2$—CO$_2$H and is obtained with the POZ polymerization reaction is terminated with $^-$S—CH$_2$CH$_2$—CO$_2$—CH$_3$ (followed by hydrolysis without isolation).

Various exemplary reactions illustrating the preparation via the one-step method of R$_1$-POZ-X derivatives are illustrated below. In the reactions presented below, R$_1$ and R$_7$ are methyl and Y is —OH or —NHR$_2$, where R$_2$ is CH$_3$.

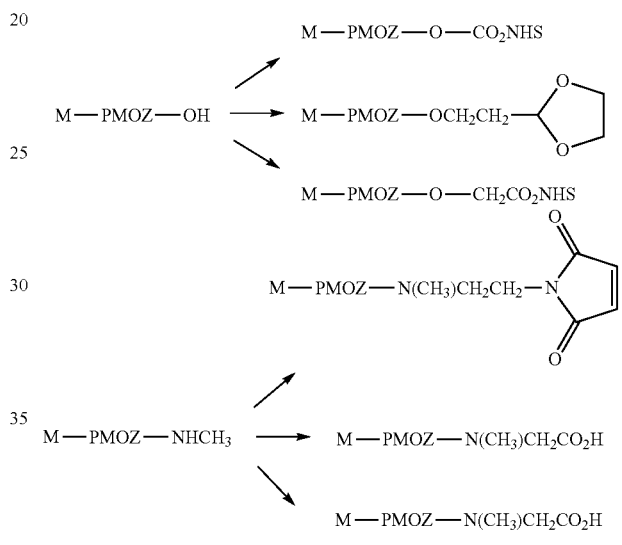

The structures above can be seen to fall within the description of Scheme 1. For example, for the active carbonate above (M-PMOZ-OCO$_2$—NHS) R$_1$ and R$_7$ are methyl, p and q are zero, and X is the succinimidyl carbonate. For the active ester above (M-PMOZ-O—CH$_2$—CO$_2$NHS) R$_1$ and R$_7$ are methyl, P is —O—, p is 1, Q is —CH$_2$—, q is 1, and X is —CO$_2$NHS.

The monofunctional POZ derivatives with the active groups described above provide a number of useful and differing properties, allowing for the selection of a particular monofunctional POZ derivative with a desired functional active group based on the nature of the target molecule and the desired reaction conditions. For example, when the functional active group is an aldehyde, the monofunctional POZ derivative reacts predominately with the N-terminal amine of the target molecule in a defined pH range to form an imine (which is typically reduced with borohydride to a secondary amine). When the functional active group is an active ester, the monofunctional POZ derivative reacts predominately with amines, including, but not limited to, non-terminal lysine groups on the target molecule. Likewise, when the functional active group is an active carbonate or tresylate, the monofunctional POZ derivative reacts readily with amines, but with reaction conditions and selectivity different from active esters and aldehyde. Furthermore, when the functional active group is a vinylsulfone or maleimide the monofunctional POZ derivative reacts predominately with thiols, but the reaction conditions differ for each of these groups, providing a range of reaction conditions appropriate for a range of target molecules.

Importantly, each of the monofunctional POZ derivatives formed using the synthetic scheme above is capable of forming a hydrolytically stable target molecule-POZ conjugate.

Building Block Two-Step Method

In an alternative embodiment, a two-step synthesis method is disclosed. In the first step of the two-step method, an initial polymer product ($R_1$-POZ-Y, below), prepared by polymerization as described above, is reacted with a desired compound to produce a POZ intermediate ($R_1$-POZ-Y', below). In the second step of the two-step method, this POZ intermediate is further reacted with a range of compounds comprising a range of functional active groups to form a series of monofunctional POZ derivatives ($R_1$-POZ-X, below) capable of forming hydrolytically stable target molecule-POZ conjugates. The two-step synthetic method offers the advantage of providing a range of monofunctional POZ derivatives using only two reactions and starting from a single initial polymer product ($R_1$-POZ-Y), thus minimizing the need to optimize polymerization conditions for multiple polymer products. The two-step method provides monofunctional POZ derivatives not available by the one-step method. In its most general form, the transformations of the building block two-step method are illustrated in Scheme 2 below.

Scheme 2

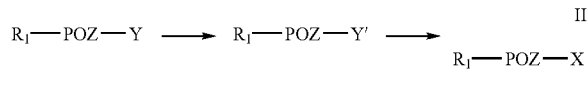

II

The building block two-step method can be presented in a detailed form as follows in Scheme 3. In Scheme 3, Y' is an active group, including, but not limited to, active esters and active carbonates, capable of reacting with a functional nucleophile, represented by the T group.

Scheme 3

III

Step 1

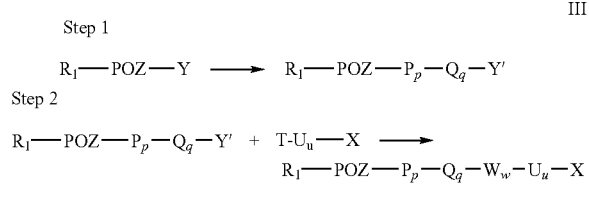

Step 2

Where $R_1$-$R_4$, $R_7$, $R_8$, $R_{11}$, $R_{14}$-$R_{15}$, $R_{23}$, POZ, P, Q, k, m, n, p, q, Y, and X are as described above;

U is a linking group; U can be any group capable of forming the linkages shown in scheme 3 and may be selected depending on the chemistry of the groups with which it forms a linkage; representative U groups include, but are not limited to, including, but not limited to —($R_{16}$)$_o$—, —($CR_5R_6$)$_o$—, —NH—$R_{21}$—NHCO—$R_{22}$—;

o is an integer from one to ten;

w and u are integers independently selected from one or zero;

$R_5$, $R_6$, $R_{16}$, $R_{21}$ and $R_{22}$ are each independently selected from hydrogen or unsubstituted or substituted alkyl, alkenyl or aralkyl groups, in one embodiment having from 1 to 10 carbon atoms;

$R_{17}$ is selected from hydrogen or unsubstituted or substituted alkyl, alkenyl or aralkyl group groups, in one embodiment having from 1 to 10 carbon atoms, or substituted or unsubstituted aryl groups.

Y' and T are a reactive pair that react to form a linkage W which is hydrolytically stable, wherein the Y' and T reactive pair and the resulting W linkage are selected from those groups and linkages shown in Table 1. Y' and T groups may be reversed without affecting the nature of the W linkage.

TABLE 1

Some possible T-Y' pairs and resulting W linkages

| T group | Y' Group | W Linkage |
|---|---|---|
| —$NH_2$ | Any active carbonate (such as, but not limited to, —O—CO—O—Z) | Urethane (—NH—CO—O—) |
| —OH | isocyanate (—NCO) | Urethane (—NH—CO—O—) |
| —$NH_2$ | any active ester or acid halide (such as, but not limited to, —CO—O—Z, —CO—Cl and —CO—Br) | Amide (—NH—CO—) |
| —$NH_2$ | NCO | Urea (—NH—CO—NH—) |
| —NCS | —$NH_2$ | Thiourea (—NH—CS—NH—) |
| halides —Cl or —Br | —OH | Ether (—O—) |
| —OH | —$OSO_2$—$R_{17}$ | Ether (—O—) |
| halides | —SH | Thioether (—S—) |
| O—$SO_2$—$R_{17}$ | —SH | Thioether (—S—) |
| halides | —$NH_2$ | Amine (—NH—) |
| O—$SO_2$—$R_{17}$ | —$NH_2$ | Amine (—NH—) |
| —SH | —NCO | —S—CO—NH— |
| —SH | —$OSO_2$—$R_{17}$ | Thioether (—S—) |

An exemplary reaction illustrating the preparation of a hydrolytically stable $R_1$-POZ-$P_p$-$Q_q$-$W_w$-$U_u$-X derivative is illustrated below. In this reaction $R_1$ is hydrogen and $R_7$ is methyl, Y is —OH, p and q are zero, U is —$CH_2CH_2$—, u is one, the reactive pair T and Y' are —$NH_2$ and —O—$CO_2$—NHS, respectively, which form the urethane W linkage, w is one, and X is an acetal (protected aldehyde):

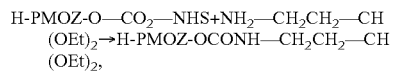

which after hydrolysis, yields

Another example of Scheme 3 is illustrated below. In this reaction $R_1$ and $R_7$ are methyl, Y is —OH, P is —O—, p is one, Q is —$CH_2CH_2$—, q is one, the reactive pair T and Y' are —$NH_2$ and —$CO_2H$, respectively, which form the amide (—CONH) W linkage, w is one, U is —$CH_2CH_2$—, u is one, and X is acetal (protected aldehyde):

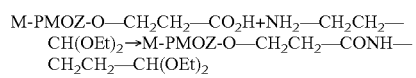

which after hydrolysis, yields

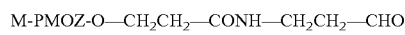

As discussed above, each of the active functional groups of Scheme 3 has unique advantages and specificities in reacting with target molecules. Furthermore, the reactivity of the T and Y' groups towards one another may be controlled through the nature of the Q and U groups. By increasing the chemical distance between the T and Y' and/or the T and X groups by increasing the size of the Q and U groups as described, the reactivity of the Y' and T groups is altered. Furthermore, the reactivity of the active functional group X towards the target molecule may be similarly modulated.

As with the one-step method, each of the monofunctional POZ derivatives formed using the two-step synthetic scheme above is capable of forming hydrolytically stable target molecule-POZ conjugates.

The Living-Polymer Method

In a further alternative embodiment of the invention, small, reactive molecules may be used to terminate oxazoline polymerization to directly provide monofunctional POZ derivatives, which can react with target molecules to form a hydrolytically stable target molecule-POZ conjugate. This method is referred to as the living polymer method. The living polymer method can be presented in its most general terms as follows in Scheme 4:

Scheme 4

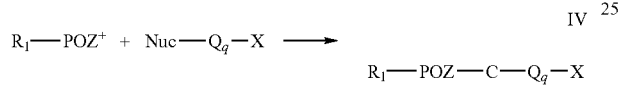

Where $R_1$-$R_4$, $R_7$, $R_8$ and $R_{14}$-$R_{15}$, $R_{23}$, POZ, Q, k, m, n, q, Y, and X are as described above;

$POZ^+$ represents the cation $—[N(COR_7)CH_2CH_2]_n^+$ formed during oxazoline polymerization;

$R_{19}$ is selected from hydrogen or unsubstituted or substituted alkyl, alkenyl or aralkyl group groups, in one embodiment having from 1 to 10 carbon atoms; and Nuc is a nucleophile capable of terminating the living POZ polymerization reaction by interacting with the terminal cation $—N(COR_7)CH_2CH_2^+$ to form the hydrolytically stable linkage C, wherein the Nuc group and the resulting C linkage can be selected from those groups and linkages shown in Table 2.

TABLE 2

Some possible Nuc groups and C linkages

| Nuc Group | C Linkage |
|---|---|
| —$NHR_{19}$ | Amine (—$NR_{19}$—) |
| —SH | Thioether (—S—) |
| —$NH_2$ | Amine (—NH—) |
| piperazine | Part of ring structure |
| piperidine | Part of ring structure |

An exemplary reaction illustrating the preparation of the $R_1$-POZ-C-$Q_q$-X derivative is given below. In the reaction presented below, $R_1$ and $R_7$ are methyl, Nuc is —$NH_2$, C is —NH—, Q is —$CH_2$—, q is one, and X is —$CO_2H$ (note that the methyl ester is hydrolyzed during the reaction below):

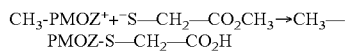

Contrary to the suggestions in the art, the present disclosure shows that cation trapping with alkoxides, such as —O—$CH_2$—$CO_2$—$CH_3$, does not result in the desired product.

As stated in Table 2, the C linkage is incorporated into the piperazine and piperidine ring structure when these compounds are used as the Nuc group. Examples of the C linkage and the structures resulting from using piperazine and piperidine as the Nuc group are provided below.

In one embodiment of this reaction, a mercaptide compound is used to terminate the oxazoline polymerization. In this method, oxazoline polymerization is initiated as described herein to form a POZ polymer with an oxazolinium cation at the terminating end of the POZ polymer. The reaction is terminated by adding a nucleophilic mercaptide molecule to the reaction, thereby terminating the living POZ polymerization. The mercaptides molecule comprises an active functional group (the active functional group may be protected as described herein) capable of reaction with a group on a target molecule to form a hydrolytically stable linkage.

In a specific embodiment of this method, the mercaptides has the structure $R_{25}S$-$D_d$-X, wherein:

X is as defined above;

$R_{25}$ is a metal; in one embodiment, $R_{25}$ is Li, Na or K;

D is a linking group, including but not limited to, an unsubstituted or substituted alkyl, alkenyl, heterocyclyl or aryl group, —$(CH_2)_b$—CONH—$(CH_2)_b$—, —NH—$(CH_2)_b$—NHCO—$(CH_2)_b$, —CO—$(CH_2)_b$—, —CO—$C_6H_4$—, or —CO—$R_{26}$, or —$(CR_{27}R_{28})_b$;

$R_{27}$ and $R_{28}$ are each independently selected from hydrogen or unsubstituted or substituted alkyl, alkenyl or aralkyl group groups, in one embodiment having from 1 to 10 carbons;

$R_{26}$ is —$C_6H_{10}$—$CH_2$— (cyclohexylmethylene);

d is 0 or 1; and b is an integer from 1 to 10.

In one embodiment, the active functional group is a protected functional group or a compound that may be converted to an active functional group. As discussed above, each of the active functional groups has unique advantages and specificities in reacting with target molecules. As above, each of the monofunctional POZ derivatives formed using the synthetic scheme above is capable of forming a hydrolytically stable target molecule-POZ conjugate.

Specific POZ Derivatives

The present disclosure describes a variety of monofunctional POZ derivatives which can be prepared by the methods described above. Furthermore, the present disclosure describes a number of compounds useful in the synthesis of the monofunctional POZ derivatives of the present disclosure.

In one embodiment, the monofunctional POZ derivatives are described by the general formula (I), (III) or (IV):

Wherein the definitions in the general formulas (I), (II) and (III) are as provided for above with reference to Schemes 1-4.

In addition, a number of specific structures for the monofunctional POZ derivatives of the present disclosure are provided below. These structures are listed for exemplary purposes only and are not meant to limit the scope of the monofunctional POZ derivatives described herein. As above, when referred to below, the definitions provided in Schemes 1-4 above are applicable to the structures below; the definitions below also apply where applicable. In addition, for all the structures provided below, the $R_1$ group is understood to be included at the position of the initiator group (to the left of the POZ group).

$R_9$ is a linking moiety such as —$(R_{16})_O$— or —NH—$R_{21}$—NHCO—$R_{22}$—;

G is an unsubstituted or substituted aryl group or a substituted or unsubstituted alkyl, alkenyl or alkynyl group, such as, but not limited to, a fluoroalkyl group; and Ar is an unsubstituted aryl or substituted aryl group.

In one embodiment, the present disclosure provides for monofunctional POZ derivatives made by the building block one-step method. Exemplary structures derived by this route include, but are not limited to, the following structures.

POZ-P—$(CR_3R_4)_m$—CH(OR$_{14}$)$_2$

POZ-P—$(CR_3R_4)_m$—CHO and POZ-NHCO—C$_6$H$_4$—CHO

POZ-P—$(CR_3R_4)_m$—CO$_2$H

POZ-P—$(CR_3R_4)_m$—CO—Z

POZ-P—$(CR_3R_4)_m$—CO—NH—NH$_2$

POZ-O$_2$C—O—Z

POZ-O—SO$_2$-G

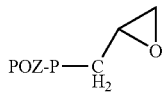

POZ-P—CH$_2$CH$_2$—SO$_2$—CH=CH$_2$ and POZ-NHCO—C$_6$H$_4$—SO$_2$—CH=CH$_2$

POZ-NH—CO—C$_6$H$_4$—NHCO—CH$_2$—I

POZ-P—$(CR_3R_4)_n$—CCH

In another embodiment, the present disclosure provides for monofunctional POZ derivatives made by the building block two-step method utilizing nucleophilic displacement on a POZ sulfonate ester (an intermediate derived from POZ-OH):

POZ-N$_3$

POZ-P—$(CR_3R_4)_n$—CH(OR$_{14}$)$_2$

POZ-P—$(CR_3R_4)_n$—CHO

POZ-OCN

POZ-SCN

POZ-CN

POZ-P—$(CR_3R_4)_n$—CCH

POZ-P—$(CR_3R_4)_n$—CO$_2$H and POZ-P—$(CR_3R_4)_n$—CO—Z

POZ-P—Ar—CO$_2$H and POZ-P—Ar—CO—Z

In another embodiment, the present disclosure provides for monofunctional POZ derivatives made by the building block two-step method utilizing nucleophilic displacement on a POZ active carbonate (an intermediate derived from POZ-OH):

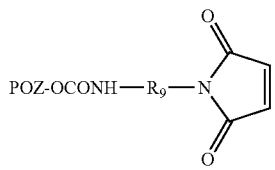

POZ-OCONH—$(CR_3R_4)_n$—CO$_2$H

POZ-OCONH—$(CR_3R_4)_n$—CO—Z

POZ-OCONH—C$_6$H$_4$—CHO

In another embodiment, the present disclosure provides for monofunctional POZ derivatives incorporating maleimides made by nucleophilic substitution on any of the above active esters:

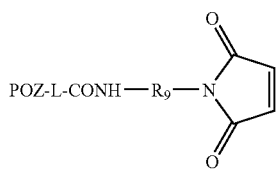

Where

POZ-L-CO— is derived from any of the herein described active carboxylate esters; and L is any of the linking moieties shown above that link POZ to the carboxyl group and includes —P—$(CR_3R_3)_m$—, —P—Ar—, and pyridinium —NC$_5$H$_4^+$—.

These maleimides can be seen to fit the above POZ-$P_p$-$Q_q$-$W_w$—$U_u$—X formula in which L comprises the $P_p$-$Q_q$ segment, —CONH— comprises the $W_w$ segment, and $R_9$ comprises the $U_u$ segment.

In another embodiment, the present disclosure provides for POZ derivatives made by the living cation method utilizing nucleophilic attack on the POZ cation generated during polymerization of 2-alkyl-2-oxazoline:

POZ-P—$(CR_3R_4)_n$—CO$_2$H

POZ-P—Ar—CO$_2$H and POZ-P—Ar—CO—Z

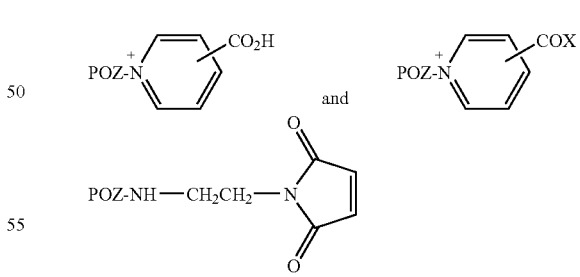

All of the above POZ derivatives react with a group on a target molecule to form a hydrolytically stable linkage between the target molecule and the PO derivative.

Specific POZ Derivatives from Piperidines or Piperazines

As discussed herein, the living POZ cation can be terminated with a substituted or unsubstituted piperidine or piperazine or derivatives of the foregoing. The substitutions include, but are not limited to, those groups described with respect to a substituted alkyl and substituted and unsubstituted alkyl, alkenyl, aralkyl or heterocycloalkyl. These POZ derivatives are difficult to illustrate with the above Schemes 1-4 because the linking group, designated C in Scheme 4, is part of the piperidine or piperazine ring structure. For example, the POZ cation can be trapped with 4-piperidine methanol to yield a POZ alcohol, with 4-piperidine butyric acid to yield a POZ carboxylic acid, or with piperazine itself to yield a POZ amine:

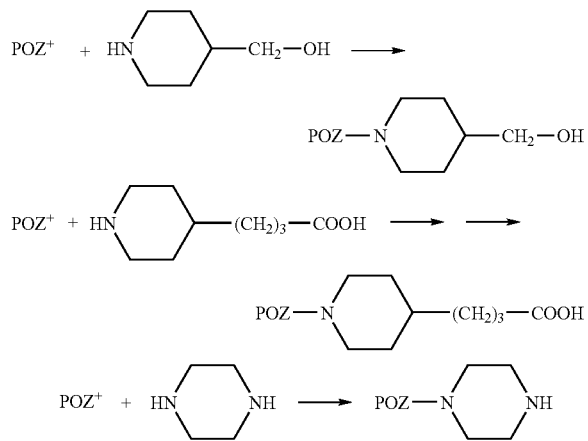

Terminations with such piperidines and piperazines are useful because the strong nitrogen nucleophile gives rapid and clean termination to introduce a terminal functional active group. At least four piperidine and piperazine derivatives are commercially available, including 1-piperazinepropanol, 4-piperidine butyric acid, 3-piperidine carboxylic acid and 4-piperidine methanol, and others could be readily synthesized.

It is to be understood that any of the POZ derivatives described above which are prepared from POZ alcohols, acids or amines could be prepared from such piperidines or piperazines in which the nitrogen-containing ring provides the alcohol, acid or amine. For example, the following compounds can be prepared from the above POZ terminated with 4-piperidine methanol:

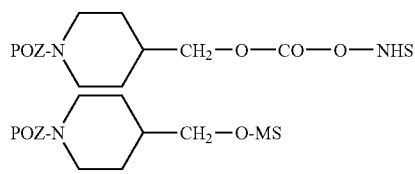

These compounds in turn could be converted to a range of useful derivatives including acetals, maleimides, and active esters:

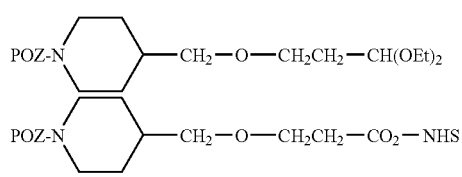

-continued

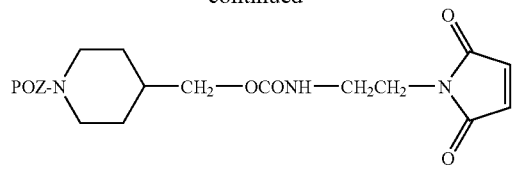

Use of the POZ Derivatives

The described monofunctional POZ derivatives, through the functional active groups, may be used to produce a hydrolytically stable target molecule-POZ conjugate. In addition, using the monofunctional POZ derivatives described herein, one target molecule is bound by each POZ derivative. In other words, there is no more than 1 target molecule bound to each POZ derivative. The variety of functional active groups present in the monofunctional POZ derivatives allow for the monofunctional POZ derivatives to be coupled to a variety of groups on the target molecule using a variety of reaction chemistries. For example, when the functional active group is an aldehyde, the monofunctional POZ derivative reacts predominately with N-terminal amines of a target protein molecule in a defined pH range. When the functional active group is an active ester, the monofunctional POZ derivative reacts predominately with amines, including, but not limited to, lysine groups on a target molecule. Likewise, when the functional active group is an active carbonate or tresylate, the monofunctional POZ derivatives react with amines, but with reaction conditions and selectivity different from active esters and aldehyde. Furthermore, when the functional active group is a vinylsulfone, maleimide or iodoacetamide, the monofunctional POZ derivative reacts predominately with thiols, but the reaction conditions differ for each of these groups, providing a range of reaction conditions appropriate for a range of target molecules.

Importantly, each of the monofunctional POZ derivatives formed using the synthetic scheme above is capable of forming hydrolytically stable target molecule-POZ conjugates.

In one embodiment, the target molecule is a polypeptide, such as, but not limited to, a protein. For example, a monofunctional POZ derivative may be coupled to the therapeutically important protein, such as, but not limited to, granulocyte colony stimulating factor (GCSF). This exemplary reaction is illustrated schematically below by the following reaction:

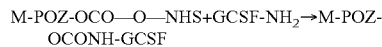

In this embodiment, the amine shown on GCSF represents one of the several available lysine groups.

Similarly GCSF contains an available thiol group, and under the proper conditions a monofunctional POZ derivative with maleimide as the functional active group can react with this thiol group.

Active POZ derivatives can be coupled to peptides as well. For example, a monofunctional POZ derivative with an active ester as the functional active group can couple to the available amino groups on insulin:

In an alternate embodiment, the target molecule is a small molecule, drug or a diagnostic agent.

Target Molecule-POZ Conjugates

The present disclosure describes a variety of monofunctional POZ derivatives capable of forming a linkage with a target molecule to produce a hydrolytically stable target molecule-POZ conjugate as discussed above. In a general embodiment, the present disclosure provides for a hydrolytically stable target molecule-POZ conjugate having the general formula (IV):

A-B-TM  (IV)

Wherein,
A is a monofunctional POZ derivative described herein, minus any leaving groups eliminated during the reaction of the functional active group on the POZ derivative with a binding partner on the target molecule;
TM is a target molecule; and
B is a hydrolytically stable linkage formed between the functional active groups of a monofunctional POZ derivative of the present disclosure and a binding partner on the target molecule, it being understood that the nature of the hydrolytically stable B linkage will depend on the nature of the active functional group on the monofunctional POZ derivative and the binding partner on the target molecule. Exemplary functional active groups, binding partners and B linkages are provided in Table 3 below. The listing in Table 3 is not meant to be exhaustive and other combinations and resulting B linkages may be envisioned given the teachings of the present disclosure.

TABLE 3

| Functional active group | Binding Partner on target Molecule | B linkage |
|---|---|---|
| Tresylate | SH | Thioether (—S—) |
| Maleimide | SH | Thioether (—S—) |
| Active carbonate | $NH_2$ | Urethane (—NH—CO—O—) |
| Active ester | $NH_2$ | Amide (—NH—CO—) |
| Aldehyde | $NH_2$ (amine) | Amine (—NH—) |

EXAMPLES

Reagents

Reagents were purchased from EM Science or Aldrich and distilled before use. Chlorobenzene and oxazolines were distilled from calcium hydride. Gel permeation chromatography (GPC) was performed on an Agilent Technologies machine with an 1100 quaternary pump and an RI detector. Two Phenogel™ GPC columns (Phenomenex, 5μ, 500 A°, 300×7.8 mm) were used in series in a column heater (60° C.). The mobile phase was 100% N,N'-dimethylformamide (DMF) at a flow rate of 1 mL/min. A calibration curve was generated with M-PEOZ-OH samples of different molecular weights as determined by MALDI (750, 1K, 2K, 5K and 10K). Gel filtration chromatography (GFC) was performed with the same system utilizing a Shodex KW-803 column, with 1 mM HEPES, pH 7.0 buffer as mobile phase. A UV detector was used to monitor 228 nm. MALDI-TOF MS was performed with a Bruker, Microflex™ instrument using dithranol as matrix. NMR was performed on a Varian 500 MHz instrument.

Example 1

Typical State-of-the-Art Preparation of M-PEOZ-OH 2000

Methyl triflate (0.113 mL, 0.001 mol) was added to a solution of 2-ethyl-2-oxazoline (2.02 mL, 0.020 mol) in acetonitrile (3.0 mL, 6.7M), and the solution stirred for 10 minutes. The reaction was then heated to 80° C. and stirred for 18 hours. Sodium carbonate (1.167 g) and water (1 mL) were added and the resulting mixture was heated overnight at 90° C. After cooling to room temperature, the mixture was diluted with methylene chloride (40 mL) and then decanted into a separatory funnel. Water (5 mL) and brine (3 mL) were added and shaken. The bottom layer was discarded, and the aqueous layer was extracted twice with methylene chloride (2×20 mL). The combined organic layers were dried over magnesium sulfate, filtered and concentrated by rotary evaporation. The crude oil was dissolved in acetone and precipitated by drop-by-drop addition to diethyl ether (80 mL). The resulting powder was dried by vacuum (1.90 g, 94% yield).

GPC showed a single peak with an appreciable high-MW shoulder (Mn=3600 Da, 9%) (FIG. 2A). The main peak had a Mn of 1980 Da, PD 1.1. NMR showed the expected peaks (see Example 6). MALDI-TOF MS gave a set of peaks with a maximum at 2000 Da, PD 1.04 and 99.1 Da separation. The MALDI spectrum also showed a second set of peaks with 99.1 Da separation, but with each peak 14 Da less than the main set. The maximum for this set of peaks occurred at 1600 Da.

Example 2

Second State-of-the-Art Preparation of M-PEOZ-OH 2000

Chlorobenzene (6.9 mL), acetonitrile (2.3 mL) and methyl triflate (0.164 mL, 1.5 mmole) were mixed at ambient temperature under nitrogen. 2-Ethyl-2-oxazoline (3.05 mL, 3.0 g, 30 mmole) was then added slowing with stirring. The mixture was heated to 70° C. and stirred for 8 hours. The reaction mixture was then cooled to room temperature by immersion in an ice bath. Potassium hydroxide (2 mmol) in 1 mL of methanol was added and the mixture stirred for one hour. The mixture was then extracted with methylene chloride (40 mL). The methylene chloride layer was separated and washed three times with water (40 mL total). The organic layer was dried, filtered and concentrated by rotary evaporation to 5 mL. The product was precipitated by addition to diethyl ether (100 mL) and dried under vacuum (yield 0.7 g).

Figure 2B:
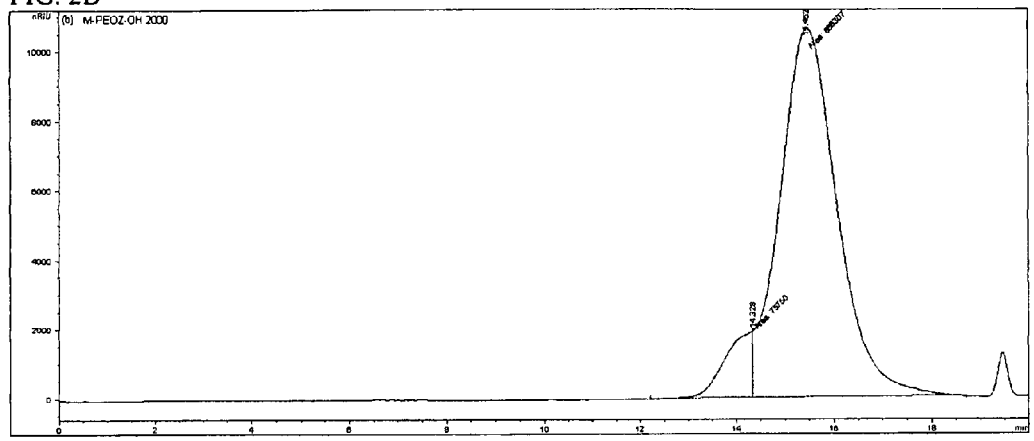

GPC showed a single peak with an appreciable high-MW shoulder (Mn=3300 Da, 6%) (FIG. 2B). The main peak had a Mn of 2200 Da, PD 1.07. NMR showed the expected peaks (see Example 6). MALDI-TOF MS gave a set of peaks with a maximum at 2300 Da, and 99.1 Da separation. The MALDI spectrum also showed a second set of peaks with 99.1 Da separation, but with each peak 14 Da less than the main set. The maximum for this set of peaks occurred at 2100 Da.

Example 3

Effect of Ethyldiisopropylamine on M-PEOZ+Termination

Methyl triflate (0.0566 mL, 0.5 mmol) was added to a solution of 2-ethyl-2-oxazoline (1.01 mL, 10.0 mmol) in chlorobenzene (5 mL, 2M) at room temperature, and the solution stirred for 10 minutes. The solution was then heated to 110° C. and stirred for 30 minutes. The solution was cooled to 0° C. and diisopropylethylamine (0.261 mL, 1.5 mmol) was added and the resulting mixture was stirred for 18 hours at 50° C. The mixture was cooled to room temperature and added drop-by-drop into diethyl ether (50 mL) to give a white precipitate. The solid was dried under vacuum in almost quantitative yield.

GPC showed two peaks, one at approximately 2000 Da (24%) and one at approximately 3800 Da (76%). The MALDI spectrum confirmed the presence of both high- and low-MW products.

Example 4

Effect of 2,6-Lutidine on M-PEOZ$^+$ Termination

Methyl triflate (0.0424 mL, 0.375 mmol) was added to a solution of 2-ethyl-2-oxazoline (0.758 mL, 7.5 mmol) in chlorobenzene (3.75 mL) at room temperature, and the solution stirred for 10 minutes. The solution was then heated to 110° C. and stirred for 30 minutes. The solution was cooled to 0° C. and 2,6-lutidine (0.170 mL, 1.5 mmol) was added and the resulting mixture was stirred for 18 hours at 50° C. The mixture was cooled to room temperature and added drop-by-drop into diethylether (20 mL) to give a white precipitate. The solid was dried under vacuum in almost quantitative yield.

GPC showed two peaks, one at approximately 2000 Da (89%) and one at approximately 4000 Da (11%) consistent with some dimerization. The NMR spectrum showed peaks at 4.2 and 5.0 ppm, consistent with the presence of unterminated oxazolinium cation.

Example 5

Attempted Termination of Oxazoline Polymerization with Methyl Glycolate

Methyl triflate (0.453 mL, 0.004 mol) was added to a solution of 2-ethyl-2-oxazoline (4.04 mL, 0.040 mol) in chlorobenzene (5 mL, 2M) at room temperature, and the solution stirred for 10 minutes. The solution was then heated to 110° C. and stirred for 30 minutes. The solution was cooled to 0° C. and 2,6-lutidine (0.929 mL, 0.008 mol) and methyl glycolate (0.609 mL, 0.008 mol) were added and the resulting mixture was stirred for 18 hours at room temperature. The mixture was cooled to room temperature and added drop-by-drop into diethyl ether (1500 mL) to give a white precipitate. The solid was dried under vacuum in almost quantitative yield.

The NMR showed peaks at 4.46 and 4.99 ppm, consistent with oxazolinium ion and consistent with failure of the glycolate to terminate polymerization.

Example 6

Preparation of M-PEOZ-OH 2000 Under Optimal Conditions

Chlorobenzene (30 mL) and MeOTf (344 μL, 3.0 mmol) were mixed at room temperature under nitrogen and added to 2-Et-2-Ox (6.06 mL, 60 mmol) in 20 mL of chlorobenzene. The mixture was stirred for 35 minutes with heating to 110° C. The mixture was next cooled to 0 C and then a solution of sodium carbonate (2.12 g) in 40 mL of water was added and stirred overnight. The mixture was poured into a separatory funnel and 40 mL of water was added. The bottom layer was removed and the aqueous layer was extracted with methylene chloride (3×60 mL). The combined organic layers were dried over magnesium sulfate, filtered and concentrated by rotary evaporation. The thick oily residue as dissolved in 7 mL methylene chloride and added drop-by-drop to diethyl ether (80 mL) at 0° C. This precipitation was repeated to provide 4.2 g of a white powder (84% yield).

NMR (Varian, 500 MHz, 10 mg/mL CDCl$_3$) shows the usual backbone peaks at 1.12 μm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OH) appears at 3.8 ppm (s). GPC showed a single peak, with no high MW shoulder and no appreciable tailing; Mn=1900 Da, and polydispersity (PD)=1.03 (FIG. 3A). MALDI gave a spectrum with Mn=1900 Da, and 99.1 Da mass units of separation. The calculated PD was 1.03.

p-Nitrophenyl Carbonate derivatization. The product was converted into the p-nitrophenyl carbonate, which was then purified and hydrolyzed in the presence of 0.2N NaOH solution (pH 8). Measurement of the p-nitrophenol (UV absorption at 400 nm, $\epsilon$=18,000 M$^{-1}$cm$^{-1}$) gave degree of —OH substitution as 99%.

Example 7

Preparation of M-PEOZ-OH 5000 Under Optimal Conditions

Chlorobenzene (80 mL) and MeOTf (354 μL, 3.2 mmole) were mixed at room temperature under nitrogen in a one-necked 250 mL round bottom flask. 2-Et-2-Ox (16.4 mL, 16.0 g, 160 mmol) was added slowly into the flask with stirring. The mixture became cloudy upon addition of oxazoline. The mixture was heated at 42° C. and stirred for one h. As the mixture warmed it became clear. The mixture was then heated to 80° C. and stirred for 3.75 h. The mixture was next cooled to room temperature by immersing in an ice bath for 15 min.

The polymerization was terminated by the addition of 40 mL of water and 2 g of sodium carbonate, followed by stirring for 30 mins. The aqueous layer was separated and the organic layer was once again extracted with 40 mL of water and 1 g of sodium carbonate followed by stirring for 30 mins. The aqueous layer was separated and combined with the first aqueous layer, and the combined aqueous solution was stirred overnight at room temperature. The cloudy aqueous layer (~80 mL) was then acidified with 0.5 M HCl (~40 mL) until the pH was less than 6 (pH paper) and a clear solution was obtained.

The polymer was then extracted 4 times with methylene chloride (200 mL each time) and the combined organic layers were dried with anhydrous magnesium sulfate for one hour with stirring. The methylene chloride solution was evaporated under vacuum, and the resulting residue was dissolved into 25 mL of dry methylene chloride and precipitated by drop-by-drop addition to 250 mL ethyl ether (room temperature). The resulting white solid was then dried overnight in a vacuum oven at 50° C. The dried material was a white powder (14.1 g, 88% yield).

NMR (Varian, 500 MHz, 10 mg/mL CDCl$_3$) shows the usual backbone peaks at 1.12 μm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OH) appears at 3.8 ppm (s). GPC GPC showed a single peak with retention time of 13.5 min. Mn=4100 Da, and polydispersity (PD)=1.06. Mn (theoretical)=4980 Da. A small shoulder at 12.4 min indicates a high MW impurity of about 1%; Mn=8900 Da (FIG. 3B). MALDI gave a spectrum with Mn=4910 Da, and 99.1 Da mass units of separation. The PD was 1.02. p-Nitrophenyl Carbonate derivatization. The product was converted into the p-nitrophenyl carbonate, which was then purified and hydrolyzed in the presence of 0.2N NaOH solution (pH 8). Measurement of the p-nitrophenol (UV absorption at 400 nm, $\epsilon$=18,000 M$^{-1}$cm$^{-1}$) gave degree of —OH substitution as 99%.

Example 8

Synthesis of POZ p-nitrophenyl Carbonate

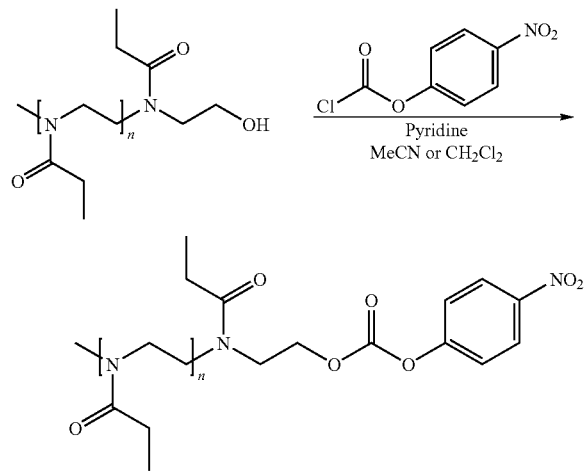

A solution of M-PEOZ-OH (10.0 g, 1.0 mmol) in 80 mL of acetonitrile was concentrated using rotary evaporation. The residue was dissolved in methylene chloride (40 mL) and p-nitrophenylchloroformate (1.61 g, 7.96 mmol) was added at 0° C. Pyridine (0.80 mL, 9.95 mmol) was added, drop by drop, and the mixture stirred at room temperature for three hours. The mixture was concentrated using rotary evaporation and then added to diethyl ether to give a white precipitate. Solvent was decanted and the precipitate was dried under vacuum. The product was dissolved in slightly acidic water, stirred for 20 minutes and filtered. The product was extracted in methylene chloride and dried over magnesium sulfate. The solution was concentrated by rotary evaporation and precipitated by addition to diethyl ether. The solvent was decanted and the product dried under vacuum. Yield 8.7 g. NMR (Varian, 500 MHz, 10 mg/mL CDCl$_3$) shows the usual backbone peaks at 1.12 ppm (s, 3H, CH$_3$CH$_2$CO—); 2.31 ppm (small m) and 2.41 ppm (large s) (total area 2H, CH$_3$CH$_2$CO—); 3.47 μm (s, 4H, —NCH$_2$CH$_2$N—); 7.38 ppm (d, 2H, J=5.2 Hz); and 8.29 ppm (d, 2H, J=5.2 Hz). The initiating methyl peak appears as two singlets at 2.9 ppm (small) and 3.03 ppm (large) (CH$_3$—NCH$_2$CH$_2$). The terminal methylene (—CH$_2$—O—CO—) appears at 4.42 ppm (s). p-Nitrophenyl Carbonate substitution. The product was hydrolyzed in the presence of 0.2N NaOH solution. Measurement of the free p-nitrophenol (UV absorption at 400 nm, ε=17,000 M$^{-1}$cm$^{-1}$) gave degree of —OH substitution of 100%.

Example 9

Synthesis of M-PEOZ Amine

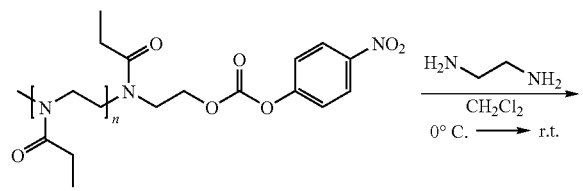

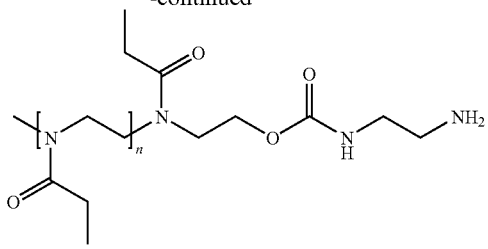

A solution of M-PEOZ-PNPC (3.60 g, 0.694 mmol) in methylene chloride (20 mL) was cooled to 0° C. and ethylene diamine (2.33 mL, 34.7 mmol) was added. The solution was stirred for one hour in the cold and then 18 hours at room temperature. The mixture was concentrated using rotary evaporation, diluted by addition of n-butyl alcohol (20 mL) and the alcohol then removed by rotary evaporation (to remove the diamine azeotropically). The residue was dissolved in methylene chloride and added to diethyl ether. The solvent was decanted and the white powder dissolved in methylene chloride (100 mL). The solution was washed with 1N NaOH solution. The aqueous phase was washed twice with methylene chloride (2×70 mL), and the organic layers combined and dried over magnesium sulfate. The solution was filtered, concentrated and added to ethyl ether. The solvent was decanted and the white powder dried under vacuum. NMR (Varian, 500 MHz, 10 mg/mL CDCl$_3$) shows the usual backbone peaks at 1.12 ppm (s, 3H, CH$_3$CH$_2$CO—), 2.31 ppm (small s) and 2.41 ppm (large s) (total area 2H, CH$_3$CH$_2$CO—), and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OCO—NH—) appears at 4.2 ppm (br s, 2H) and the protons associated with ethylene diamine appear at 2.82 ppm (m, 2H, —NH—CH$_2$—CH$_2$—NH$_2$) and 3.23 ppm (m, 2H, —NH—CH$_2$—CH$_2$—NH$_2$).

Example 10

Synthesis of POZ Succinimidyl Carbonate

A solution of M-PEOZ-OH (0.5 g, 0.23 mmol) was prepared in 5 mL of dry dichloromethane or dry acetonitrile and concentrated by rotary evaporation. A suspension was prepared of disuccinimidyl carbonate (0.24 g, 0.9 mmol) in 5 mL of dry dichloromethane or dry acetonitrile. Pyridine (0.094 mL, 1.16 mmol) was added to this suspension. The M-PEOZ-OH solution was added to the above suspension, drop by drop, and the mixture was stirred overnight at room temperature. The mixture was filtered, concentrated using rotary evaporation, and then added to diethyl ether. The solvent was decanted and the white powder dried under vacuum. The powder was dissolved in dry acetone and precipitated by addition to diethyl ether. Yield 0.6 g. NMR (Varian, 500 MHz, 10 mg/mL CDCl$_3$) shows the usual backbone peaks at 1.12 ppm (s, 3H, CH$_3$CH$_2$CO—); 2.31 ppm (small m) and 2.41 ppm (large s) (total area 2H, CH$_3$CH$_2$CO—); 3.47 ppm (s, 4H, —NCH$_2$CH$_2$N—); 2.70 ppm (s, 4H, SC group). The initiating methyl peak appears as two singlets at 2.9 ppm (small) and 3.03 ppm (large) (CH$_3$—NCH$_2$CH$_2$). The terminal methylene (—CH$_2$—O—CO—) appears at 4.24 ppm (s).

Example 11

Synthesis of M-PEOZ-T-COOH 2000 a. Synthesis of Methyl Ester

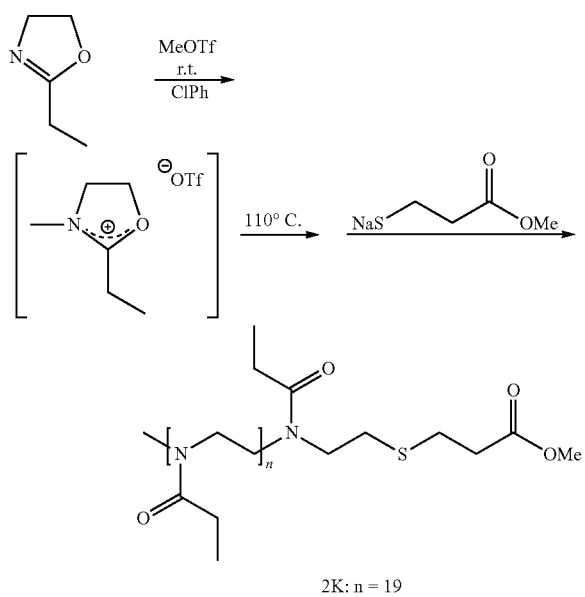

2K: n = 19

A solution of 1 mmol of M-PEOZ+ was prepared in chlorobenzene as described above. The solution was cooled to room temperature. Methyl 3-mercaptopropionate (0.65 mL, 6 mmol) was added drop by drop to a suspension of NaH (0.12 g, 5 mmol) in THF at 0° C. The M-PEOZ+ solution was then added slowly to the THF solution. The resulting mixture was warmed to room temperature and stirred overnight. The reaction mixture was filtered and added to ether to get a white precipitate. The solvent was decanted and the solid dried under vacuum to give 1.5 g of a white powder.
NMR (Varian, 500 MHz, 10 mg/mL $CDCl_3$) shows the usual backbone peaks at 1.12 ppm (s, 3H, $CH_3CH_2CO$—); 2.31 ppm (small m) and 2.41 ppm (large s) (total area 2H, $CH_3CH_2CO$—); 3.47 ppm (s, 4H, —$NCH_2CH_2N$—). The initiating methyl peak appears as two singlets at 2.9 ppm (small) and 3.03 ppm (large) ($CH_3$—$NCH_2CH_2$). The terminal methylene (—$CH_2$—COO—$CH_3$) appears at 2.64 ppm (s), its neighboring methylene (S—$CH_2$—$CH_2$—CO—) appears at 2.81 ppm (s) and the methylene adjacent to the sulfur group (—$CH_2$—S—$CH_2$—) appears at 2.71 ppm (s). The methyl ester group (—$CH_2$—COO—$CH_3$) appears as a sharp singlet at 3.71 ppm.
Synthesis of Thioacid
A solution of ester from above (8.1 g, 0.004 mol) in 20 mL methanol was prepared and mixed with 30 mL of a 0.05N NaOH solution (0.02 mol). The mixture was stirred at room temperature for 40 min and then acidified with 5% HCl. The methanol was removed by rotary evaporation and the solution extracted with dichloromethane. The extract was dried over magnesium sulfate, filtered, concentrated, and precipitated by addition to ether. The ether was decanted and the residue dried under vacuum. The NMR spectrum showed the disappearance of the methyl ester peak at 3.71 ppm. GPC showed a high MW shoulder of 6%. The main peak gave Mn 1870 Da, PD of 1.15. The above sample was purified by ion-exchange chromatography using a DEAE Sepharose FF medium. GPC of the product gave a single main peak with no high-MW shoulder, with Mn 1970 Da and PD 1.08. MALDI gave Mn 2090 Da and PD of 1.04.

Example 12

Synthesis of M-PEOZ-T-Propionic Acid (M-PEOZ-T-PA) 1000

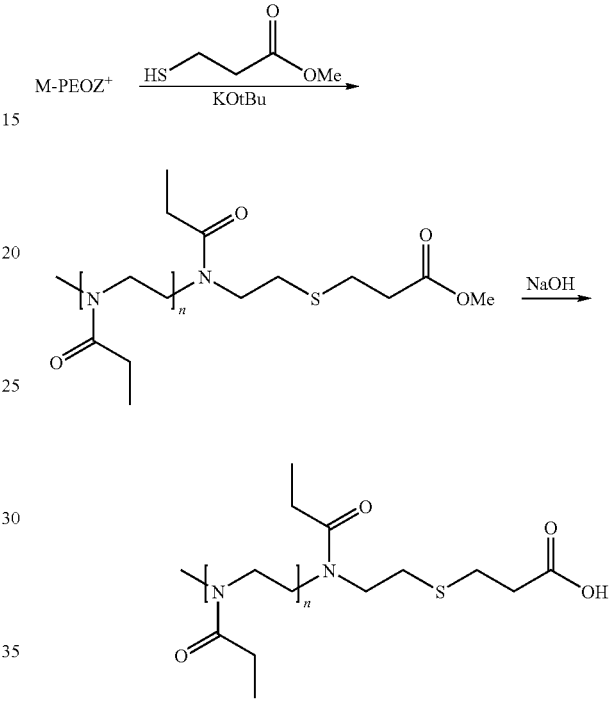

M-PEOZ+ was prepared using 2-ethyl-2-oxazoline (5.05 mL, 50 mmol) and methyl triflate (0.63 mL, 5.56 mmol) in chlorobenzene (25 mL), as described above. To obtain the terminating reagent, methyl 3-mercaptopropionate (2.41 mL, 22.2 mmol) was added dropwise into a suspension of potassium tert-butoxide (1.25 g, 11.1 mmol) in chlorobenzene (10 mL) at 0° C. After the mixture was stirred for 2 hours in the cold, the solution of M-PEOZ+ in chlorobenzene was added dropwise. The mixture was stirred in the cold for 4 hours and then stirred for 18 hours at room temperature. Water (50 mL) was added and the mixture was acidified (pH ~3) by the addition of 5% aqueous HCl solution. Volatiles including chlorobenzene were removed using rotary evaporation. The resulting aqueous solution was treated with a solution of NaOH (1.33 g, 33.3 mmol) in $H_2O$ (70 mL). After stirring for 1 hour, the mixture was acidified with 5% aqueous HCl solution and then extracted with dichloromethane. The combined organic phases were dried over sodium sulfate, filtered, concentrated, and precipitated by addition to ether. The ether was decanted and the residue was dried under vacuum. Further purification was performed by ion-exchange chromatography using a DEAE Sepharose FF medium. GPC and GFC show a single peak, with Mn 910 Da and PD of 1.02. MALDI gave Mn 1100 Da and PD of 1.05.

Example 13

Synthesis of M-PEOZ-T-Propionic Acid NHS Ester (M-PEOZ-T-SPA)

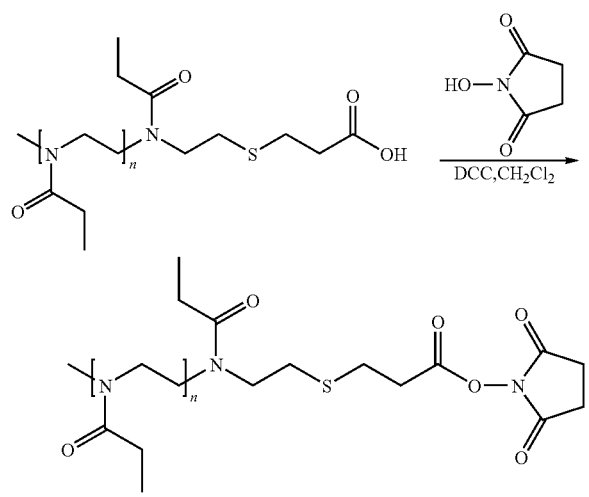

N-hydroxysuccinimide (0.467 g, 2.26 mmol) and DCC (0.467 g, 2.26 mmol) were added to a solution of M-PEOZ-T-CO$_2$H from the above preparation (Mn 910 Da, 2.0 g, 2.20 mmol) in dichloromethane (44 mL) at 0° C. After stirring for 2 hours in a cold, the mixture was warmed to room temperature and stirred overnight. The mixture was filtered using a syringe filter and the filtrate added to diethyl ether to give a white powder. The product was collected by vacuum filtration and dried under vacuum (2.0 g, 89% yield). Attachment of the succinimidyl group was demonstrated by $^1$H NMR spectra showing the succinimidyl protons at 2.86 ppm (s, 2H) in addition to the usual backbone peaks. To determine yield, the compound (calc. Mn 1025 Da, 0.4 g, 0.39 mmol) was treated with phenylethylamine (0.15 mL, 1.17 mmol) and triethylamine (0.16 mL, 1.17 mmol) in dichloromethane (4 mL). After stirring overnight, the mixture was filtered and added to diethyl ether. The white powder was filtered and dried using vacuum. According to gel filtration chromatography, the conversion yield was 99%.

Example 14

Synthesis of M-PEOZ-thio-NH$_2$ Via Mercaptide

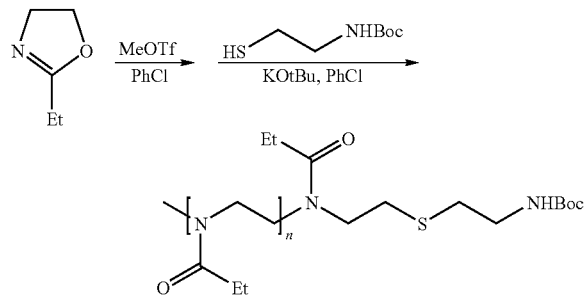

Synthesis of tBoc Ester

Methyl triflate (0.283 mL, 0.0025 mol) was added into a solution of 2-ethyl-2-oxazoline (5.05 mL, 0.05 mol) in chlorobenzene (25 mL). After the stirring for 10 minutes at room temperature, the mixture was heated to 110° C. for 30 minutes followed by cooling down to 0° C. To obtain a terminating reagent, Boc-cysteamine (0.84 mL, 0.0075 mol) was added dropwise into a suspension of potassium tert-butoxide (0.561 g, 0.005 mol) in chlorobenzene (5 mL) at 0° C. After the mixture was stirred for 1 hour in the cold to give a clear solution, the solution of M-PEOZ$^+$ in chlorobenzene was added dropwise using a syringe at 0° C. The mixture was stirred in the cold for 4 hours and then stirred for 18 hours at room temperature. The mixture was slowly added to diethyl ether to give a white precipitate. The ether was decanted and the residue was dissolved in water followed by extraction with dichloromethane. The combined organic layers were dried over sodium sulfate, filtered, concentrated, and precipitated by addition to ether. The mixture was filtered and the resulting white powder was dried under vacuum to give 4.0 g of targeted compound in 87% yield.

NMR (Varian, 500 MHz, 10 mg/mL CDCl$_3$) shows the usual backbone peaks at 1.12 ppm (s, 3H, CH$_3$CH$_2$CO—); 2.31 ppm (s) and 2.41 (s) (total area 2H, CH$_3$CH$_2$CO—); and 3.47 ppm (s, 4H, —NCH$_2$CH$_2$N—). The initiating methyl peak appears as two singlets at 2.9 ppm and 3.03 ppm (CH$_3$—NCH$_2$CH$_2$). The Boc cysteamine terminal group peaks are at 1.44 ppm (s, 9H, —CH$_2$NHBoc), 2.67 ppm (m, 2H, —SCH$_2$CH$_2$NHBoc), 2.71 ppm (m, 2H, —CH$_2$SCH$_2$CH$_2$NHBoc), and 3.32 ppm (m, 2H, —SCH$_2$CH$_2$NHBoc). The crude mixture contains approximately 8% of M-PEOZ-OH species based on the NMR integration. GPC produces a sharp peak with a Mn=1790 Da, PD=1.07.

Synthesis of Amine

Hydrochloric acid (4 M solution in dioxane, 34.0 mL) was added into a flask containing M-PEOZ-T-NH(Boc) (Mn 1850 Da, 3.218 g, 1.74 mmol) at 0° C. with vigorous stirring. The mixture was warmed to room temperature and stirred for an hour. The mixture was concentrated by rotary evaporation and diluted with water (50 mL), and the pH was adjusted to ~13. The resulting aqueous solution was extracted with dichloromethane three times. The combined organic phases were dried over Na$_2$SO$_4$, filtered, concentrated, and precipitated into ether to give a white powder that was filtered and dried under vacuum to give 2.5 g of product. Further purification was performed by ion-exchange chromatography using a CM Sepharose FF medium. Two fractions were collected by column purification. One 0.2 g fraction contained a pure amine polymer and a second 2.2 g fraction contained the amine polymer with the 8% impurity (M-PEOZ-OH) carried over from the previous step.

$^1$H NMR (Varian, 500 MHz, 10 mg/mL CDCl$_3$) showed the usual backbone peaks at 1.14 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The initiating methyl peak appeared as two singlets at 2.9 ppm and 3.03 ppm (CH$_3$—NCH$_2$CH$_2$). The terminal cysteamino group peaks were found at 2.69 ppm (m, 4H, —SCH$_2$CH$_2$NH$_2$, —CH$_2$SCH$_2$CH$_2$NH$_2$), and 2.91 ppm (m, 2H, —SCH$_2$CH$_2$NH$_2$). The removal of the Boc group was confirmed by the disappearance of the peak at 1.44 ppm (s, 9H, —CH$_2$NHBoc). GPC showed an Mn value of 1700 Da with PDI of 1.10.

Example 15

Synthesis of M-PEOZ-T-SCM (M-PEOZ-S—CH$_2$—CO$_2$—NHS)

Synthesis of Acid

Chlorobenzene (100 mL) and 2-ethyl-2-oxazoline (39.7 g, 0.4 mole, 50 eq.) were mixed under argon and stirred for 30 minutes at 0° C. Methyl triflate (1.31 g, 1 eq.) was added into the flask with stirring, and stirring was continued at 0° C. for 30 min., 25° C. for 30 min, 42° C. for 1 h, and then at 80° C. for 3.5 h. The mixture was cooled to room temperature. The termination mixture was prepared in a separate flask by mixing potassium t-butoxide (2.25 g, 5 eq.) and methyl 2-mercaptoacetate (2.9 g, 6 eq.) and chlorobenzene (100 mL) and stirring at 0° C. for 1 h. The polymerization mixture was added to the termination mixture and stirred overnight at room temperature. The mixture was diluted with methylene chloride (50 mL), filtered and added into diethyl ether (750 mL). The supernatant was decanted and the precipitate collected and dried under vacuum for 1 hour. The powder was dissolved in 100 mL of 0.1M NaOH and stirred for 4 h. The mixture was acidified by addition of 25 mL of 0.5M HCl. The aqueous solution was extracted with methylene chloride (150 mL×3 times), dried over MgSO4, concentrated to 50 mL, and precipitated into diethylether (400 mL). The resulting white powder was dried under vacuum.

The resulting acid was purified by DEAE ion exchange chromatography to yield pure acid (as shown by GFC chromatography). NMR showed that the methyl and methylene peaks of the ester at 1.30 and 4.19 ppm, respectively, had disappeared.

Synthesis of NHS Ester

N-hydroxysuccinimide (0.139 g, 1.21 mmol) and DCC (0.249 g, 1.21 mmol) were added to a solution containing M-PEOZ-T-CM (M-PEOZ-S—CH$_2$—CO$_2$H, Mn 4970 Da, 6.0 g, 1.21 mmol) dissolved in dichloromethane (60 mL) at 0° C. After stirring for 2 hours at this temperature, the clear colorless mixture was warmed to room temperature and stirred overnight. The mixture with a white precipitate was filtered with the aid of a syringe filter. The filtrate was added to diethyl ether with stirring to produce a white powdery precipitate. The residue was collected using a sintered glass funnel and dried under vacuum to give 5.2 g of the desired product (85% yield).

H$^1$-NMR: The attachment of hydroxysuccinimide was verified by $^1$H NMR spectra that showed the succinimidyl protons at 2.87 ppm (s, 4H) in addition to the usual backbone peaks for PEOZ.

To determine conversion yield, this compound (calc. Mn 5070 Da, 0.100 g, 0.0197 mmol) was treated with phenethylamine (0.012 mL, 0.0987 mmol) and triethylamine (0.014 mL, 0.0987 mmol) in dichloromethane (2 mL). After stirring overnight, the mixture was filtered and added into diethyl ether. The white powder was filtered and dried using vacuum to give the desired amide in quantitative yield. According to GFC, the conversion yield was 95+%.

Example 16

Hydrolysis Rate of Thio NHS Esters

The reactivity of the thio NHS esters M-PEOZ-T-SCM 5K and M-PEOZ-T-SPA 5K were evaluated in pH 8 borate buffer. Accurately weighed samples of both esters were placed in 100 mL volumetric flasks and dissolved in pH 8 borate buffer (0.2M). Aliquots from each flask were taken initially every 1 minute and later every 10 minutes, and assayed by UV-spectrophotometry at a λmax absorbance of 260 nm. The rate at which the absorbance value increased was plotted against time. From these calculations the rate at which 50% of the maximum absorbance value was determined. The calculated t ½ for M-PEOZ-T-SCM 5K and M-PEOZ-T-SPA 5K were <1 minute and 15 minutes, respectively.

Example 17

Conjugation of M-PEOZ-OCO$_2$—NHS with GCSF

The monofunctional derivative M-PEOZ-OCO$_2$—NHS was conjugated to a target molecule, in this example GCSF, as described below. Four mg of GCSF (0.215 μmol, MW=18.6 kDa), dissolved into 1 ml of 0.2 M sodium borate buffer (pH 8.5), was reacted for 60 min at room temperature with 3 equivalents per amino group of GCSF (a total of 5 lysine plus the α-amine) of M-PEOZ-OCO$_2$—NHS. Under these reaction conditions, the reaction between the monofunctional POZ derivative and the amino groups on GCSF occurs primarily at the more exposed nucleophilic amines.

Modification of GCSF was analysed by RP-HPLC employing an analytical C18 Agilent column equilibrated in 60% buffer A (HPLC grade H$_2$O containing 0.05% TFA,) and eluted with a 1% buffer B/min (70% CH$_3$CN and 0.05% TFA) linear gradient over 30 min at a flow rate of 1 ml/min. Eluted material was detected by absorbance at 280 nm. The GCSF-POZ conjugate is eluted as a non symmetrical peak at a retention time of 18.8 min, which suggests heterogeneity of the GCSF-POZ conjugate in terms of the number of POZ molecules conjugated to the GCSF molecule. The Habeeb assay for amino group content indicated that 70% of the protein amino groups were no longer free.

The formation of several conjugates was confirmed by SDS-PAGE and by size exclusion HPLC. SDS-PAGE experiments were carried out using a Pharmacia Phast System. The minigels (12% polyacrylamide) were run at a constant voltage (200V) and prepared according to the method of Laemmli. For protein staining the gel was put into a Coomassie blue solution, while for polymer staining a barium iodine solution was used. Polymer staining is based on the formation of a barium iodine complex (Kurfust M. M., 1992, *Analytical Biochemistry*, 200, 244-248). The SDS-PAGE data showed several bands, indicating that a mixture of chemically different molecular GCSF conjugated were obtained, with such conjugates comprising one, two or three POZ molecules.

Size-exclusion HPLC analysis was conducted using an analytical Biosep SEC 52000 column eluted with an isocratic mobile phase of 0.1 M sodium phosphate, 0.2 M sodium chloride, pH 7.2, and 20% acetonitrile at a flow rate of 0.5 ml/min. Eluted material was detected by absorbance at 280 nm. The chromatograms show an elution peak at 5.75 min corresponding to higher molecular weight than the native protein (elution peak at 9.00 min), indicating that the GCSF-POZ conjugate was formed.

Example 18

Conjugation of M-PEOZ-OCO$_2$—NHS with Ribonuclease A

The monofunctional POZ derivative M-PEOZ-OCO$_2$—NHS was conjugated to a target molecule, in this example ribonuclease A (RNAse A), as described below. 5 mg of RNAse A (0.36 μmol, MW 13 KDa), dissolved into 1 ml of 0.2 M sodium borate buffer (pH 8.5), was reacted with 3 equivalents per amino group of RNAse A (a total of 5 lysines plus the α-amine) of M-PEOZ-OCO$_2$—NHS. The reaction was carried out for 60 min at room temperature. The extent of RNAse A modification was analysed by RP-HPLC employing an analytical C4 Agilent column equilibrated in 80% buffer A (HPLC grade H$_2$O containing 0.05% TFA) and eluted with a 1% buffer B/min (90% CH$_3$CN and 0.05% TFA) linear gradient over 30 min. at a flow rate of 1 ml/min. Eluted material was detected by absorbance at 280 nm. The chromatogram shows a small amount (<10% of unmodified protein. The peak for the POZ-modified protein was quite broad, suggesting heterogeneity of the RNAse A-POZ conjugate in terms of the number of POZ molecules conjugated to the RNAse A molecule. The Habeeb assay for amino group content indicated that 26% of the amino groups on RNAse A were modified.

The formation of several conjugates was confirmed by SDS-PAGE and by size exclusion HPLC. SDS-PAGE experiments were carried out using a Pharmacia Phast System and stained as described in above Example. As with the GCSF results, SDS-PAGE data showed several bands, indicative of several different RNAse A-POZ conjugates. Size-exclusion HPLC analysis was conducted using an analytical Biosep SEC S2000 as described in the above Example. The chromatogram shows an early broad peak corresponding to higher molecular weight with respect to the native protein, consistent with formation of an RNAse A-POZ conjugate.

Example 19

Preparation of M-PEOZ-Maleimide and Orthopyridyldisulfide

In this example, the monofunctional POZ derivative M-PEOZ-maleimide was prepared by from M-PEOZ-NH$_2$ (above). To 100 mg (0.55 mmol, 3 eq) of 4-maleimidobutyric acid were added 126 mg of HOBT (1.09 mmol) and 226 mg of DCC (1.09 mmol) in anhydrous chloroform. After 3 hours, this was followed by the addition of 16 mg (0.00254 mmol) of M-PEOZ-NH$_2$. The resulting solution was maintained at room-temperature overnight. The reaction mixture was washed with 0.1N HCl, dried, and evaporated in a vacuum. Ethyl ether was added and the precipitate was collected by filtration and dried. The yield of the reaction was of 65%.

The orthopyridyldisulfide (OPSS) reagent was prepared in a like fashion by coupling succinimidyl propionic acid dithiopyridine (SPDP) (3 times excess) with M-PEOZ-NH$_2$ for 5 hours in chloroform at room temperature in the presence of triethylamine (3 eq.). The final product was precipitated from ether and obtained in 65% yield.

Example 20

Comparison of Reaction of M-PEOZ-Maleimide, M-PEOZ-OPSS, PEG-Maleimide and PEG-OPSS with Thiols To evaluate the reactivity of M-PEOZ-maleimide and M-PEOZ-OPSS and to compare the reactivities of the M-PEOZ-maleimide and M-PEOZ-OPSS derivatives with their corresponding PEG derivatives, the PEOZ and PEG polymers were conjugated to the cysteine-containing tripeptide glutathione. The reaction with glutathione was monitored with Ellman's assay as is known in the art. A solution of 20 mM of the PEOZ or PEG derivative and 2 mM thiol was prepared in 0.1 M phosphate buffer pH=7 (containing 5 mM EDTA). Aliquots (30 μl) were withdrawn and quenched by addition to 920 μl of pH 7 buffer. Fifty microliters of DTNB were added, and after 5 min the absorbance at 420 nm was measured to evaluate the remaining thiol. The degree of cysteine modification is reported in Table 4.

TABLE 4

| Conjugate | Degree of thiol modification |
| --- | --- |
| M-PEOZ-maleimide | 58% |
| PEG- maleimide | 73% |
| M-PEOZ -OPSS | 27% |
| PEG-OPSS | 10% |

Example 21

Hydrolysis and Aminolysis Studies of M-PEOZ-p-Nitrophenyl Carbonate and PEG-p-Nitrophenyl Carbonate The rates of hydrolysis of M-PEOZ-p-nitrophenyl carbonate and the corresponding PEG-p-nitrophenyl carbonate, were evaluated by following UV absorbance of the p-nitrophenol released in borate buffer 0.1 M pH 8 at 412 nm at room temperature or the reactivity of polymers towards amines. In this example, a solution of Gly-Gly (ratio Gly-Gly/polymer 1:1) was added to activated PEOZ or PEG solution. Table 5 reports the hydrolysis and aminolysis rates as a half life.

TABLE 5

| Activated Polymer | Hydrolysis pH 8 Half-life (min.) | Aminolysis by Gly-Gly pH 8 Half-life (min.) |
| --- | --- | --- |
| M-PEOZ-p-nitrophenyl carbonate | 31 | 19 |
| PEG-p-nitrophenyl carbonate | 40 | 25 |

Example 22

Preparation of M-PEOZ-O—CH$_2$—CO$_2$H

M-PEOZ-OH (1.5 g, 0.00024 moles, 1 eq) was azeotropically distilled in 60 ml of toluene; 30 ml of distillate was removed. The reaction mixture was slowly cooled to room temperature, followed by the addition of 0.5 ml (0.5 mmol) of a 1.0 M solution of potassium t-butoxide in t-butanol. The resulting mixture was stirred for 1 hour at room temperature, followed by the addition of 94 mg (0.48 mmol) of t-butyl bromoacetate. The resulting cloudy mixture was heated to reflux, cooled and stirred for 18 hours at room temperature. The reaction mixture was filtered through Celite and the solvent was removed under vacuum. The residue was precipitated in ethyl ether. The product was centrifuged at 4° C., washed three times and the solvent was removed. Comparison of the t-butyl peak in NMR (1.47 ppm) with the terminal methyl peak showed quantitative conversion.

The resulting carboxylic acid t-butyl ester was dissolved in a mixture of CH$_2$Cl$_2$/trifluoroacetic acid/water (50 ml/0.1 ml/100 ml) and the solution was stirred at room temperature for 3 hours. The solvent was then removed under vacuum to completely remove the TFA, followed by centrifugation in ethyl ether to yield 900 mg of product (60%). NMR showed that the t-butyl peak had been removed, and a new methylene peak at 4.08 ppm was observed.

The carboxylic acid was purified from excess M-PEOZ-OH by anionic exchange chromatography. 900 mg of product was loaded in a pre-equilibrated column (QAE 50) at flow rate of 1 ml/min. Isocratic elution using water was carried out until the M-PEOZ-OH was completely eluted. The solvent was changed with 0.01 N NaCl, and the product was collected. Fractions were examined by $I_2$ assay. Fractions were concentrated under vacuum at 30 ml and washed six times with $CH_2Cl_2$ (40 ml×6). The yield was 600 mg.

Example 23

Preparation of M-PEOZ-O—$CH_2$—$CO_2$—NHS

M-PEOZ-COOH (600 mg, 0.11 mmol) was dissolved in 15 mL of dichloromethane, and N-hydroxysuccinimide (104 mg 0.9 mmol) and DCC (185 mg, 0.9 mmol) were added. The reaction mixture was left to react for 24 h, and the product precipitated by addition of ethyl ether, collected by filtration and dried. The activation degree was 85% as determined by amino group modification of glycine-glycine as substrate using TNBS for determination of residual $NH_2$ groups.

Example 24

Hydrolysis and Aminolysis Studies of M-PEOZ-O—$CH_2$—$CO_2$—NHS and PEG-O—$CH_2$—$CO_2$—NHS The rates of hydrolysis of M-PEOZ-O—$CH_2$—$CO_2$—NHS and PEG-O—$CH_2$—$CO_2$—NHS were evaluated by measuring the UV absorbance of the N-hydroxysuccinimide released in borate buffer, 0.1 M pH 8, at 260 nm at room temperature. To evaluate the reactivity of polymers towards amines, a solution of Gly-Gly (ratio Gly-Gly/polymer 1:1) was added to M-PEOZ-O—$CH_2$—$CO_2$—NHS and PEG-O—$CH_2$—$CO_2$—NHS (prepared as known in the art) solution for comparison. Table 6 reports hydrolysis and aminolysis as half lives.

TABLE 6

| Activated Polymer | Hydrolysis pH 8 Half-life (min.) | Aminolysis by Gly-Gly pH 8 Half-life (min.) |
|---|---|---|
| M-PEOZ-O—$CH_2$—$CO_2$—NHS | 6.3 | 4 |
| PEG-O—$CH_2$—$CO_2$—NHS | 7.0 | 2 |

Example 25

Conjugation of M-PEOZ-O—$CH_2$—$CO_2$—NHS with GCSF 2.5 mg of GCSF (0.134 μmol, MW=18.6 KDa), dissolved into 1 ml of 0.2 M sodium borate buffer (pH 8.5), was reacted for 60 min at room temperature with 3 equivalents of M-PEOZ-O—$CH_2$—$CO_2$—NHS per amino group on GCSF (a total of 5 lysine plus the α-amine). Under these conditions, modification occurs primarily at the more exposed nucleophilic amines.

Modification of GCSF was analysed by RP-HPLC employing an analytical C18 Agilent column. Eluent A was $H_2O$ containing 0.05% TFA and eluent B was acetonitrile containing 0.05% TFA. The flow rate was 1 ml/min and detection was at 280 nm. The gradient used was 30% B at 0 min.; 30-80% B over 30 min, 80-30% B over 3 min. The chromatogram shows that no free protein is present, and it shows a broad peak at a later retention time than free GCSF, indicating that multiple forms of GCSF-POZ are present.

The formation of several conjugates was confirmed by size exclusion HPLC. Size-exclusion HPLC analysis was conducted using an Agilent GF-250 column eluted with an isocratic mobile phase of 0.1 M sodium phosphate, 0.2 M sodium chloride, pH=7.2 and 20% acetonitrile at 0.3 ml/min. The chromatogram shows a broad elution peak corresponding to higher molecular weight GCSF-POZ conjugate conjugates with respect to the native GCSF in agreement with extensive conjugation and an increase in mass.

Example 26

Comparison of the Properties of Enzymes Modified by M-POZ-O—$CH_2$—$CO_2$—NHS and PEG-O—$CH_2$—$CO_2$—NHS To evaluate the different influence on enzyme properties as a function of polymerization with POZ derivatives of the present disclosure and corresponding PEG polymers known in the art, three different enzymes, ribonuclease A, uricase and catalase, were modified with M-PEOZ-O—$CH_2$—$CO_2$—NHS (6 kDa) and PEG-O—$CH_2$—$CO_2$—NHS (5.5 kDa). To facilitate the comparison, each enzyme was modified under similar conditions regarding polymer to enzyme ratios, buffer, pH and reaction temperature.

The conditions of enzyme modification with the POZ and PEG polymers described above were 0.2 M, pH 8.5 in borate buffer. The amount of POZ and PEG polymer used for modification was calculated on the basis of calculated total available amino groups in each enzyme. For example, ribonuclease A has a molecular weight of 13.7 kDa and 11 available amino groups; uricase has a molecular weight of 130 kDa and 100 available amino groups; and catalase has a molecular weight of 240 kDa and 112 available amino groups.

To the three enzymes solutions (2.5 mg/ml) M-POZ-O—$CH_2$—$CO_2$—NHS or PEG-O—$CH_2$—$CO_2$—NHS solid were added at room temperature at a molar ratio of polymer to protein amino groups of 2/1 and 1/1 respectively. Protein concentration of the native forms of ribonuclease, uricase and catalase was evaluated spectrophotometrically using molar extinction coefficients of $9.45 \times 10^3$, $13 \times 10^3$ and $1.67 \times 10^5$ at 280 nm, respectively. After 30 minutes, polymer-enzyme conjugates were purified from unreacted polymer and n-hydroxysuccinimide by gel filtration chromatography Sephadex G-75 column, with 0.1M phosphate buffer, pH 7.4 as eluent.

The degree of protein modification was evaluated colorimetrically by TNBS assay and expressed as percentage of conjugate amino groups to the total ones present on the protein. Enzymatic activity of native and modified enzymes was evaluated as follows: ribonuclease activity was assayed by the method of Crook et al. (Biochem J. 1960 February; 74:234-8); uricase activity was determined by the method of Mahler (Anal Biochem. 1970 November; 38(1):65-84); and catalase was assayed according to a method reported by Beers and Sizer (J. Biol. Chem. 1952 March; 195(1):133-40).

The results are provided in Table 7A-C for ribonuclease (RNAse), uricase and catalase, respectively.

| Products | $NH_2$:polymer molar ratio | % modification | % activity |
|---|---|---|---|
| Table 7A | | | |
| RNAse | n.a. | n.a. | 100 |
| POZ/RNAse | 1:1 | 23 | 50 |
| POZ/RNAse | 2:1 | 36 | 30 |

| Products | NH₂:polymer molar ratio | % modification | % activity |
|---|---|---|---|
| PEG/RNAse | 1:1 | 60 | 15 |
| PEG/RNAse | 2:1 | 80 | 10 |
| Table 7B | | | |
| Uricase | n.a. | n.a. | 100 |
| POZ/Uricase | 1:1 | 58 | 37 |
| POZ/Uricase | 2:1 | 70 | 12 |
| PEG/Uricase | 1:1 | 52 | 11 |
| PEG/Uricase | 2:1 | 61 | 8 |
| Table 7C | | | |
| Catalase | n.a. | n.a. | 100 |
| POZ/Catalase | 1:1 | 35 | 90 |
| POZ/Catalase | 2:1 | 37 | 88 |
| PEG/Catalase | 1:1 | 43 | 85 |
| PEG/Catalase | 2:1 | 46 | 79 |

Ribonuclease was found to undergo a high extent of modification and consequently higher loss of activity when modified with PEG-O—CH₂—CO₂—NHS than with respect to M-POZ-O—CH₂—CO₂—NHS. In uricase, both degree of modification and loss of activity were similar with PEG-O—CH₂—CO₂—NHS and M-POZ-O—CH₂—CO₂—NHS; however, the POZ conjugates displayed somewhat higher activity at both molar ratios tested. For catalase, the extent of modification with PEG-O—CH₂—CO₂—NHS and M-POZ-O—CH₂—CO₂—NHS was similar, and in both cases a minor loss of enzymatic activity was noted, with the POZ conjugates being more active than the PEG conjugates at both molar ratios tested.

Example 27

Conjugation of M-PEOZ-NH₂ to G-CSF with TGAse

In this example, site specific modification of G-CSF by POZ-NH₂ using the enzyme TGAse was examined. The same reaction was carried out also using PEG-NH₂ with the same reagent concentrations, as a comparison:

The monofunctional alkylamine M-PEOZ derivative was prepared starting from the product M-PEOZ-OH as described above. The TGAse-catalyzed conjugation of M-PEOZ-NH₂ and PEG-NH₂ with G-CSF was carried out in 0.1 M phosphate buffer, pH 7.2 at room temperature for 18 h using 1.6 mg G-CSF, 50 mg of either the amine, and 2 mg/ml TGAse (commercially available). Under these conditions, no significant or clear conjugation for G-CSF and M-PEOZ-NH₂ takes place (as shown by reverse phase chromatography; details above) while PEG-NH₂ gave clear conjugation, When a further 2 mg/ml of TGAse enzyme was added to the reaction mixture of M-PEOZ-NH₂, the native G-CSF protein peak was decreased and a new peak, representing the conjugate M-PEOZ-G-CSF, was observed.

Example 28

Preparation of M-PEOZ Aldehyde

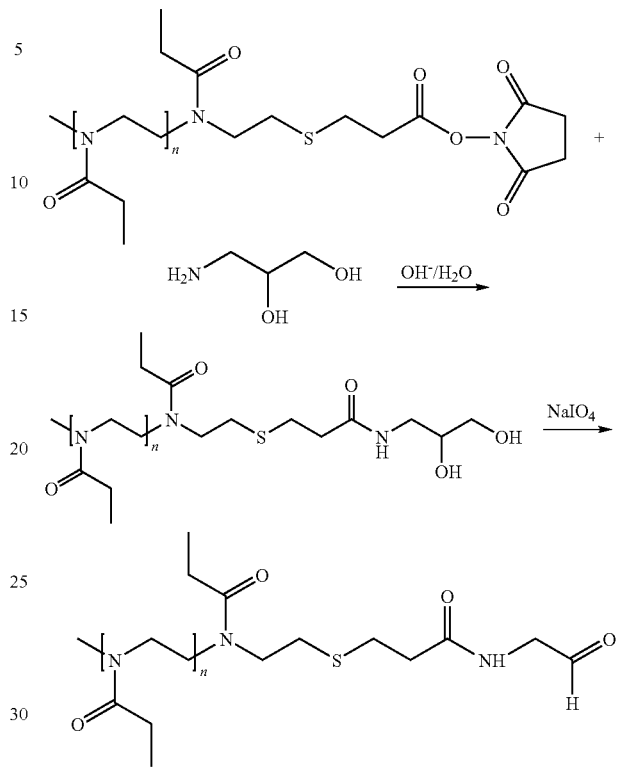

Preparation of Diol

3-Amino-1,2-propanediol (1.41 gm, 15 mmol) in 0.1 M boric acid buffer (3 mL) at pH 8.0 was prepared in a glass vial. The solution pH was adjusted to pH 9 using concentrated HCl. To this solution was added M-PEOZ NHS ester, prepared as described above (1.00 gm, 0.197 mmol) with vigorous stirring. The solution pH was maintained at 9 by addition of 1 N NaOH. The solution was allowed to stir three hours at room temperature. The solution pH was adjusted to pH 6.8 using 1N HCl. To the solution was added sodium chloride (3 gm). Water (1 mL) was added to the solution, followed by three extractions with dichloromethane (3×10 mL). The aqueous phase was discarded. The organic layer was dried over anhydrous magnesium sulfate, filtered, and concentrated by rotary evaporation. The concentrated solution was precipitated into diethyl ether (100 mL). The resulting powder was dried overnight in high vacuum. Yield: 0.7 gm. The substitution by NMR was 96%, and from GFC was 95%. NMR in DMSO-d6: —C(=O)NHCH₂CH(OH)CH₂OH: 1H, δ4.49, t; —C(=O)NHCH₂CH(OH)CH₂OH: 1H, δ4.70, d; —C(=O)NHCH₂CH(OH)CH₂OH: 1H, δ7.87, t (ill resolved).

Oxidation to Aldehyde

Diol (0.500 gm, 0.112 mmol) was dissolved in water (8 mL). The solution pH was adjusted to 6.85 by 0.1 N NaOH addition, followed by addition of sodium periodate (27.9 mg, 0.130 mmol). The solution was stirred one hour at room temperature. Water (2 mL) and NaCl (2 gm) were added to the solution. The solution was extracted three times by dichloromethane (3×10 mL). The combined organic layers were dried with anhydrous sodium sulfate. The mixture was filtered followed by concentration of the filtrate under reduced pressure. The residue was precipitated by addition to ethyl ether (50 mL). Following filtration, the resulting powder was dried under high vacuum. Yield: 0.47 gm. Mn was determined by GPC to be 4840 Da. The substitution of aldehyde was 89% based on NMR in CDCl₃.

1H-NMR in CDCl₃: —C(=O)NHCH₂CHO, 1H, δ 9.635, s; —C(=O)NHCH2CHO, 2H, δ4.175, q (poorly resolved).

Example 29

Synthesis of M-PEOZ Maleimide 2K from M-PEOZ-PNPC

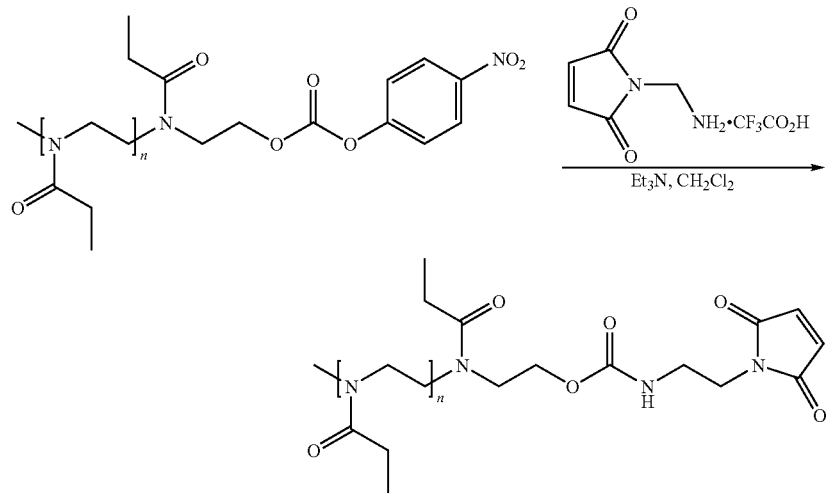

M-PEOZ p-nitrophenylcarbonate (Mn 2150 Da, 0.500 g, 0.232 mmol), prepared as described above, was added to a mixture of N-(2-aminoethyl)maleimide trifluoroacetate salt (0.065 g, 0.255 mmol) and triethylamine (0.097 mL, 0.696 mmol) in methylene chloride (5 mL). After stirring for 18 hours at room temperature, the mixture was filtered and then added dropwise into diethyl ether to give a light yellow precipitate. The solvent was decanted and the solid dried under vacuum to give quantitative yield. $^1$H NMR spectra showed the terminal methylene protons (—CH$_2$—OCO—NH—) at 4.15 ppm (br s, 2H) and the protons associated with maleimide at 6.72 ppm (s, 2H) in addition to the usual backbone peaks. The yield was determined to be ~80% by comparison of integrations of the initiating methyl group and maleimide.

Example 30

Synthesis of M-PEOZ NHS Ester Via Ethyl Isonipecotate

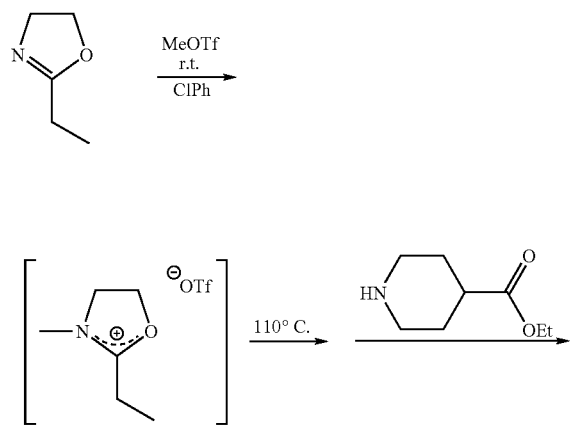

-continued

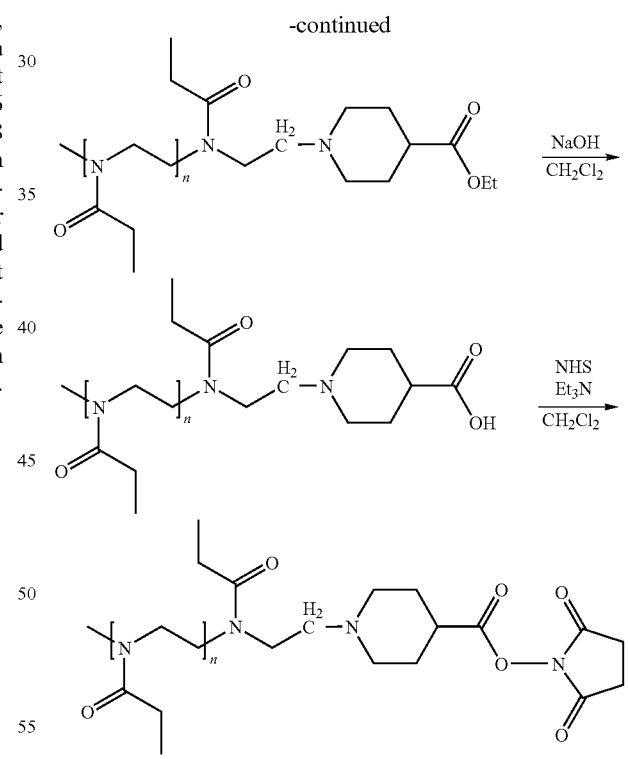

Synthesis of Ethyl Ester

Methyl triflate (2.83 mL, 25.0 mmol) was added to a solution of 2-ethyl-2-oxazoline monomer (50.47 mL, 0.500 mol) in chlorobenzene (250 mL) at room temperature. After stirring for 10 minutes, the reaction mixture was heated to 110° C. for 40 minutes. The reaction mixture was cooled to 0° C. and then ethyl isonipecotate (11.55 mL, 75.0 mmol) was added. After the resulting mixture stirred for 2 hours at room temperature, it was precipitated into ether (1500 mL) to give 57 g of a white powder. The precipitate was dissolved in 200 mL of H$_2$O and then extracted three times with 200 mL of methylene chloride. The combined organic layers were dried over MgSO₄, filtered, and concentrated under vacuum. A thick, oily residue was dissolved in CH₂Cl₂ (100 mL) and precipitated in diethyl ether (1000 mL). After the solvent was decanted, the residue was dried in vacuo to provide 43.5 g of a white powder in 86% yield. NMR (500 MHz, 10 mg/mL CDCl₃) shows the usual backbone peaks at 1.12 ppm (s, 3H, CH₃CH₂CO—); 2.31 ppm (small s) and 2.41 (large s) (total area 2H, CH₃CH₂CO—); and 3.46 ppm (s, 4H, —NCH₂CH₂N—). The initiating methyl peak appears as two singlets at 2.9 ppm (small) and 3.03 ppm (large) (CH₃—NCH₂CH₂). The piperidine peaks are showed at 1.68 ppm (br s, 3H), 1.90 ppm (br s, 2H), 2.15 ppm (br s, 2H), and 2.84 ppm (br s, 2H). The terminal ethyl ester peaks appear at 1.26 ppm (t, 3H, J=7.0 MHz, —C(=O)OCH₂CH₃) and 4.13 ppm (q, 2H, J=6.5 MHz, —C(=O)OCH₂CH₃). GPC showed Mn=1770 Da and PD=1.06. MALDI gave Mn=2050 Da and PD=1.02.

Synthesis of Acid

M-PEOZ ethyl ester (Mn=2050 Da, 10.0 g, 4.89 mmol) was dissolved in H₂O (60 mL). A solution of NaOH (0.977 g, 24.4 mmol) in H₂O (20 mL) was added and the mixture was stirred for 40 minutes. The mixture was acidified with 5% aqueous HCl solution and then extracted with dichloromethane. The combined organic phases were dried over sodium sulfate, filtered, concentrated, and precipitated by addition to ether. The ether was decanted and the residue was dried under vacuum to give 9.0 g of a white powder in 91% yield. ¹H NMR showed that ethyl ester group peaks had completely disappeared upon hydrolysis.

Synthesis of NHS Ester

N-hydroxysuccinimide (0.173 g, 1.50 mmol) and DCC (0.310 g, 1.5 mmol) were added to a solution of M-PEOZ-CO₂H (Mn 2020 Da, 3.0 g, 1.49 mmol) in dichloromethane (50 mL) at 0° C. After stirring for 2 hours in the cold, the mixture was warmed to room temperature and stirred overnight. The mixture was filtered and the filtrate was added to diethyl ether to give a white powder. The product was collected by filtration and dried under vacuum (2.8 g, 93% yield). The ¹H NMR spectrum showed the succinimidyl protons at 2.89 ppm (s, 2H) and the usual backbone peaks.

Example 31

Attempted Preparation of M-PEOZ-Mesylate

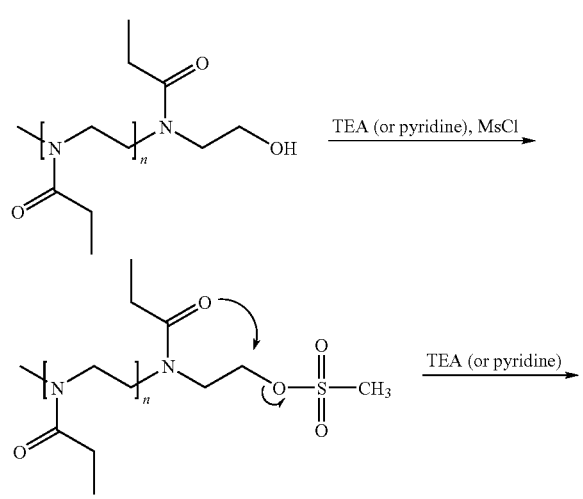

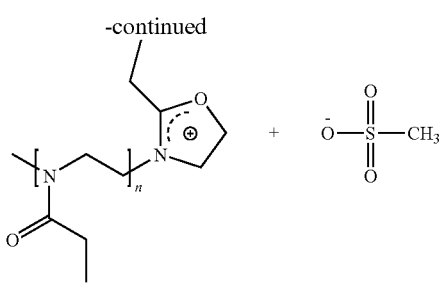

M-PEOZ-OH 2K was prepared as described above. M-PEOZ-OH 2K (1.00 gm, 0.608 mmol) was dissolved in anhydrous acetonitrile (20 mL) and evaporated to near dryness on a rotary evaporator. The residual syrup was again dissolved in acetonitrile (20 mL), and evaporated to near dryness by rotary evaporation. Anhydrous dichloromethane (5 mL) was added. Under a slow argon flow, triethylamine (169.3 µL, 1.215 mmol) followed by mesyl chloride (84.6 µL, 1.094 mmol) were added. The solution was allowed to stir at room temperature overnight under argon atmosphere. The solution was concentrated by rotary evaporation. The concentrated solution was precipitated by adding into diethyl ether. The precipitate was collected, and dried under high vacuum. Yield: 0.6 gm. NMR in CDCl₃ shows the peak of —CH₂CH₂OMs (δ4.44), but the area was consistent with only approximately 50% conversion. The low substitution of —OMs is due to side reaction to form oxazolinium ion following formation of mesylate. NMR in CDCl₃ shows peaks at δ5.01 (2H, t, five member ring that carries a positive charge: —O—CH₂CH₂N) and δ4.44 (2H, t, the same five member ring: —O—CH₂CH₂N; same shift as —CH₂—OMs).

Example 32

Synthesis of M-PPOZ-OH

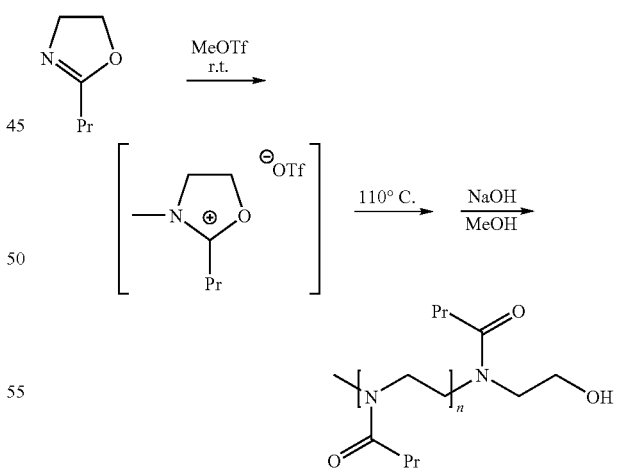

Methyl triflate (MeOTf, 25.0 µL, 0.221 mmol) was added to a solution of freshly dried and distilled 2-n-propyl-2-oxazoline (0.500 g, 4.42 mmol) mixed with freshly dried and distilled chlorobenzene (2 mL). After stirring for 10 minutes, the mixture was heated to 110° C. for 20 minutes. The mixture was cooled to 0° C. and terminated using a solution of NaOH (0.044 g, 1.11 mmol) in methanol (2 mL). NMR (500 MHz, 10 mg/mL CDCl₃) shows the backbone peaks at 0.95 ppm (s, 3H, CH₃CH₂CH₂CO—); 1.65 ppm (s, 2H, CH₃CH₂CH₂CO—); 2.25 ppm (small s) and 2.34 (large s) (total area 3H, CH₃CH₂CH₂CO—); and 3.45 ppm (s, 4H, —NCH₂CH₂N—). The initiating methyl peak appears as two singlets at 2.94 ppm (small) and 3.03 ppm (large) (CH₃—NCH₂CH₂, total area 3H). The terminal methylene (—OCH2-OH) appears at 3.8 ppm. GPC of the crude mixture showed Mn=1760 Da and PD=1.1.

Example 33

Synthesis of M-PPOZ-Thio-Propionic Acid

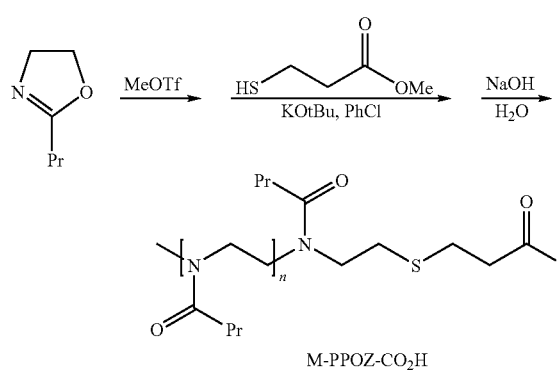

M-PPOZ-CO₂H

M-PEOZ⁺ was prepared as shown above using 2-propyl-2-oxazoline (5.66 mL, 50 mmol) and methyl triflate (0.808 mL, 7.14 mmol) in chlorobenzene (25 mL) with heating to 110° C. for 25 minutes and then cooled to 0° C. To obtain the terminating reagent, methyl 3-mercaptopropionate (3.09 mL, 28.6 mmol) was added dropwise into a suspension of potassium tert-butoxide (1.60 g, 14.3 mmol) in chlorobenzene (14 mL) at 0° C. After the mixture was stirred for 2 hours in the cold, the solution of M-PEOZ⁺ in chlorobenzene was added dropwise using a syringe. The mixture was stirred in the cold for 4 hours and then stirred for 18 hours at room temperature. Water (30 mL) was added and the mixture was acidified (pH ~3) by the addition of 5% aqueous HCl solution. Volatiles including chlorobenzene were removed using rotary evaporation. The resulting aqueous solution was diluted with H₂O (60 mL) and NaOH (1.43 g, 35.7 mmol) as a solid. After stirring for 1 hour, the mixture was acidified with 5% aqueous HCl solution and then extracted with dichloromethane. The combined organic phases were dried over sodium sulfate, filtered, concentrated, and precipitated by addition to ether. The ether was decanted and the residue was dried under vacuum to give a viscous and clear yellow oil. GPC showed a single main peak, with Mn 867 Da and PD of 1.01. GFC showed the crude product contains two different species; M-PPOZ-T-CO₂H (80%) and M-PPOZ-T-OH (20%).

Example 34

Synthesis of M-PEOZ-T-Retinoic Acid

Retinoic acid (0.0102 g, 0.0425 mmol) and hydroxybenztriazole (HOBt, 0.0115 g, 0.0849 mmol) were dissolved in acetonitrile (10 mL) and azeotroped using rotary evaporation. The residue was redissolved in dichloromethane (3 mL). DCC (0.0088 g, 0.0425 mmol) was added as a solid and the mixture was stirred for 2 hours. M-PEOZ-NH₂ 4300 Da (0.122 g, 0.0283 mmol) was added to the mixture and allowed to stir for 40 hours. The mixture was added slowly into diethyl ether to give a pale yellow powder. The product was filtered and dried to give 0.0823 g of product in 63% yield.

Example 35

Modification of Ara-C with M-PEOZ-SCM and Conjugate Activity POZ-Conjugation

M-PEOZ-O—CH₂—CO₂—NHS (M-PEOZ-SCM 5000) (180 mg, 0.034 mmol) was dissolved in 11 mL of pyridine and added to a solution of cytosine arabinose (Ara-C) (5.7 mg, 0.023 mmol), previously dissolved in 5 mL of anhydrous pyridine at 0° C. The resulting solution stirred for 72 hours at room temperature. Reverse phase HPLC (C-18 column) showed that reaction was complete. After evaporation of the solvent, the product was dissolved in methylene chloride (5 mL) and added drop by drop into 150 mL ether. The precipitate was collected by centrifugation at 4° C. and dried under vacuum. Yield 150 mg, 80%. NMR showed the usual peaks of the M-PEOZ backbone (above) plus the pyrimidine protons of Ara-C at 7.31, 7.67, 8.16, and 8.62 ppm. Exposure of the conjugate to pH 8 buffer showed that Ara-C is slowly released (15% after 24 hours), so the conjugate can be regarded as a prodrug.

Conjugate Activity

Human cervix adenocarcinoma cells (HeLa), cultured by standard procedures, were seeded into each well of a 24-well cell culture plate. After 24 hours, the culture medium was replaced with fresh medium and the cells treated with aqueous solutions of M-PEOZ-Ara-C or free Ara-C (20 mM in Ara-C) at increasing concentrations. The cells were incubated under standard conditions for 72 hours. A trypan blue assay was performed to determine cell viability. This assay revealed that the conjugated Ara-C was cytotoxic to the HeLa cells although approximately 30 times less cytotoxic than free Ara-C, consistent with the slow release process for the conjugate. Comparison to PEG-Ara-C, prepared in similar fashion, showed that the PEG- and POZ-conjugates had similar properties.

Example 36

Synthesis of H-PEOZ-S—CH₂CH₂—CO₂H

Chlorobenzene (25 mL) and 2-ethyl-2-oxazoline (9.92 g, 0.1 mol, 200 eq.) were mixed at ambient temperature under argon and cooled to 0° C. Trifluoromethane sulfonic acid (0.075 g, 1 eq.) was added with stirring, and the reaction mixture was stirred for 30 min. The mixture was then heated to 80° C. and stirred for 7 hours. The termination mixture was prepared separately by reacting potassium t-butoxide (168 mg, 3 eq.) and methyl 3-mercaptopropionate (0.360 g, 6 eq.) at 0° C. for 6 hours. The termination mixture was added to the polymerization reaction at 0° C. and then stirred overnight at room temperature. The solution was then mixed with 50 mL of 0.25M sodium hydroxide and stirred for one hour. The aqueous layer was separated, saturated with sodium chloride, and extracted with methylene chloride (250 mL×3). The methylene chloride was removed by rotary evaporation, and the polymer dried under vacuum.

The resulting acid was purified by DEAE chromatography to give 1.5 gram of white powder. Proton NMR showed the usual backbone peaks at 1.12 ppm (m, 3H, CH₃CH₂CO—), 2.31 ppm (m) and 2.41 ppm (s) (area 2H, CH₃CH₂CO—), and 3.47 ppm (m, 4H, —NCH₂CH₂N—). The propionate methylene peaks appeared at 2.74, 2.81 and 2.85 ppm. GFC revealed a single peak. GPC gave Mn 15,200 Da and PD of 1.09.

The foregoing description illustrates and describes certain embodiments of the compounds and applications of the present disclosure. Additionally, the disclosure shows and describes only the exemplary embodiments of the compounds and applications, but as mentioned above, it is to be understood that the teachings of the present disclosure are capable of use in various other combinations, modifications, and environments and is capable of changes or modifications within the scope of the concepts as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All references cited herein are incorporated by reference as if fully set forth in this disclosure.

What is claimed:

1. A terminally activated polyoxazoline compound having the general structure $R_1$—$[N(COR_7)CH_2CH_2]_n$—$S$-$Q_q$-$X$, wherein X is an active functional group capable of forming a hydrolytically stable linkage with a target molecule to form a target molecule-POZ conjugate wherein all the linkages between the target molecule and the POZ compound are hydrolytically stable in a biological system;

Q is an optional linking group;

$R_1$, and is hydrogen or an unsubstituted or substituted alkyl, alkenyl or aralkyl group;

$R_7$ is independently selected for each repeating unit from an unsubstituted or substituted alkyl, alkenyl or aralkyl group;

n is an integer from 3 to 1000; and q is zero or one.

2. The compound of claim 1 where the active functional group is protected.

3. The compound of claim 1 where $R_7$ has from 1 to 12 carbon atoms.

4. The compound of claim 1 where $R_7$ is methyl, ethyl or n-propyl.

5. The compounds of claim 1 where the active functional group is selected from the group consisting of aldehydes, active carbonates (—O—CO—Z), maleimides, sulfonate esters (OSO$_2$—$R_{23}$), hydrazide, epoxides, iodoacetamides, alkynes, azides, isocyanates, cyanates isothiocyanates, thiocyanates, nitriles, carbonyldiimidazole derivatives, vinylsulfones, carboxylic acid halides, active esters (—CO—Z) and carboxylic acids, wherein any of the foregoing may be substituted or unsubstituted, Z is an activating group and $R_{23}$ is an unsubstituted or substituted alkyl, alkenyl, alkynyl, aralkyl or aryl group.

6. A target molecule POZ conjugate of the general formula A-B-TM, wherein

A is a terminated POZ compound of claim 1, minus any leaving groups eliminated during the reaction of the active functional group on the POZ compound with a binding partner on a target molecule;

TM is the target molecule, said target molecule containing the binding partner; and B is a linkage that is hydrolytically stable in a biological system that is formed between the active functional group and the binding partner.

7. The conjugate of claim 6 wherein the active functional group is a maleimide, the binding partner is SH and B is a thioether linkage.

8. The conjugate of claim 6 wherein the active functional group is an active carbonate, the binding partner is $NH_2$ and B is a urethane linkage.

9. The conjugate of claim 6 wherein the active functional group is an active ester, the binding partner is $NH_2$ and B is an amide linkage.

10. The conjugate of claim 6 wherein the active functional group is an aldehyde, the binding partner is $NH_2$ and B is an amine linkage.

11. A method of synthesizing terminally activated polyoxazoline (POZ) compound, said method comprising the steps of:

(a) initiating POZ polymerization to form a POZ polymer with a positive cation on the terminating end; and (b) terminating said POZ polymer with a mercaptide.

12. The method of claim 11 where the mercaptides comprises the structure $R_{25}S$-$D_d$-$X$ wherein X is an active functional group or a group capable of being converted to an active functional group, the active functional group capable of forming a hydrolytically stable linkage with a target molecule to form a target molecule-POZ conjugate;

$R_{25}$ is a metal;

D is a linking group; and d is 0 or 1.

13. The method of claim 12 where $R_{25}$ is Li, Na or K.

14. The terminally activated polyoxazoline compound of claim 1 having the structure:

(b) $CH_3$—$[N(COCH_2CH_3)CH_2CH_2]_n$—$S$—$CH_2CH_2$—$CO_2H$ (c) $CH_3$—$[N(COCH_2CH_3)CH_2CH_2]_n$—$S$—$CH_2$—$CO_2H$ (d) $CH_3$—$[N(COCH_2CH_3)CH_2CH_2]_n$ $S$—$CH_2CH_2$—$NH_2$ (f) $CH_3$—$[N(COCH_2CH_2CH_3)CH_2CH_2]_n$—$S$—$CH_2CH_2$—$CO_2H$ (g) $H$—$[N(COCH_2CH_3)CH_2CH_2]_n$—$S$—$CH_2CH_2$—$CO_2H$ (j)

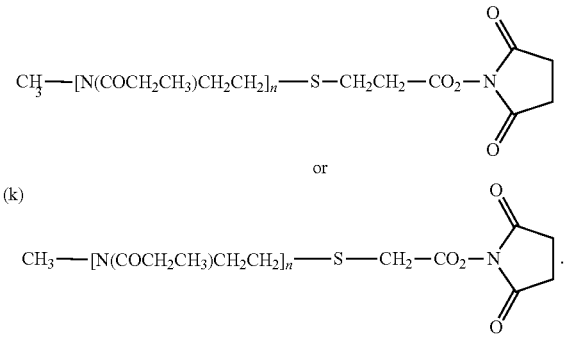

15. The compound of claim 1, wherein the linking group Q is an unsubstituted or substituted alkyl, alkenyl, aralkyl, heterocyclyl or aryl group, —$(CH_2)_m$—$CONH$—$(CH_2)_m$—, —$NH$—$(CH_2)_m$—$NHCO$—$(CH_2)_m$—, —$CO$—$(CH_2)_m$—, —$CO$—$C_6H_4$—, or —$CO$—$R_8$, —$(R_{15})_m$— or —$(CR_3R_4)_m$—, wherein m is independently an integer from 1 to 10, $R_3$, $R_4$, $R_{11}$ and $R_{15}$ are each independently selected from hydrogen or an unsubstituted or substituted alkyl, alkenyl or aralkyl group and $R_8$ is —$C_6H_{10}$—$CH_2$—.

16. The compound of claim 1 wherein the POZ polymer has a polydispersity value of less than or equal to 1.20.

17. The method of claim 12 wherein the linking group D is an unsubstituted or substituted alkyl, alkenyl, heterocyclyl or aryl group.

* * * * *